United States Patent
Mitchell et al.

(10) Patent No.: US 10,125,138 B2
(45) Date of Patent: Nov. 13, 2018

(54) TRIAZOLOTRIAZINONE DERIVATIVES HAVING ACTIVITY A S HERBICIDES

(71) Applicant: Syngenta Participations AG, Basel (CH)

(72) Inventors: Glynn Mitchell, Bracknell (GB); Linda Hazel Curley, Bracknell (GB)

(73) Assignee: SYNGENTA PARTICIPATIONS AG, Basel (CH)

(*) Notice: Subject to any disclaimer, the term of this patent is extended or adjusted under 35 U.S.C. 154(b) by 0 days.

(21) Appl. No.: 15/553,061

(22) PCT Filed: Feb. 24, 2016

(86) PCT No.: PCT/EP2016/053869
§ 371 (c)(1),
(2) Date: Aug. 23, 2017

(87) PCT Pub. No.: WO2016/135196
PCT Pub. Date: Sep. 1, 2016

(65) Prior Publication Data
US 2018/0044340 A1 Feb. 15, 2018

(30) Foreign Application Priority Data

Feb. 27, 2015 (GB) .................................. 1503365.7
Mar. 20, 2015 (GB) .................................. 1504749.1

(51) Int. Cl.
*C07D 487/04* (2006.01)
*A01N 43/90* (2006.01)

(52) U.S. Cl.
CPC ........... *C07D 487/04* (2013.01); *A01N 43/90* (2013.01)

(58) Field of Classification Search
CPC .............................. C07D 487/04; A01N 43/90
See application file for complete search history.

(56) References Cited

U.S. PATENT DOCUMENTS 6,683,081 B2 * 1/2004 Niewohner .......... C07D 487/04
514/212.08

FOREIGN PATENT DOCUMENTS

| EP | 2562174 A1 | 8/2011 |
|---|---|---|
| WO | 2012045721 A2 | 4/2012 |
| WO | 2013144231 A1 | 10/2013 |
| WO | 2014053473 A1 | 4/2014 |
| WO | 2014126070 A1 | 8/2014 |
| WO | 20141135654 A1 | 9/2014 |
| WO | 2015007662 A1 | 1/2015 |
| WO | 2015022284 A1 | 2/2015 |

OTHER PUBLICATIONS

Search Report issued in GB application No. GB1503365.7 dated Nov. 9, 2015.
International Search report issued by EPO dated Apr. 8, 2016.

* cited by examiner

*Primary Examiner* — John Pak
(74) *Attorney, Agent, or Firm* — Dinsmore & Shohl LLP; Toni-Junell Herbert

(57) ABSTRACT

The present invention relates to compounds of Formula (I), or an agronomically acceptable salt of said compounds wherein Q, $R^2$ and $R^3$ are as defined herein. The invention further relates to herbicidal compositions which comprise a compound of Formula (I), to their use for controlling weeds, in particular in crops of useful plants, and to intermediates used to synthesize said compounds.

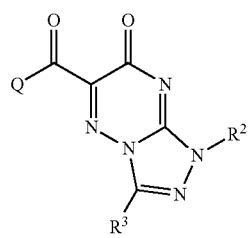

(I)

15 Claims, No Drawings

TRIAZOLOTRIAZINONE DERIVATIVES HAVING ACTIVITY AS HERBICIDES

RELATED APPLICATION INFORMATION

This application is a 371 national stage entry of International Application No. PCT/EP2016/053869 filed Feb. 24, 2016, which claims priority to GB Application No. 1503365.7 filed Feb. 27, 2015 and GB Application No. 1504749.1 filed Mar. 20, 2015, the contents of which are incorporated herein by reference herein.

The present invention relates to novel herbicidal compounds, to processes for their preparation, to herbicidal compositions which comprise the novel compounds, and to their use for controlling weeds, in particular in crops of useful plants, or for inhibiting plant growth.

Herbicidal 6-oxo-1,6-dihydropyrimidin-5-carboxamides are reported in EP-A-2562174. Herbicidal 1,2,4-triazine-3,5-dione-6-carboxamides are disclosed, for example, in WO2014/053473. Herbicidal oxopyrazine derivatives are disclosed in WO2009/016841. The present invention relates to novel herbicidal triazolotriazinone compounds.

Thus, according to the present invention there is provided a compound of Formula (I):

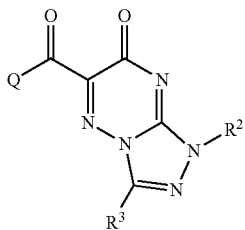

or an agronomically acceptable salt thereof,
wherein:—
Q is Q1 or Q2

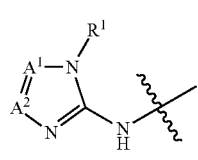 (Q1)

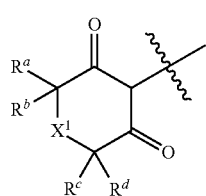 (Q2)

$A^1$ and $A^2$ are independently selected from CH and N, wherein $A^1$ and $A^2$ are not both CH;
$X^1$ is selected from the group consisting of O, C(O) and $(CR^eR^f)$;
$R^a$, $R^b$, $R^c$, $R^d$, $R^e$ and $R^f$ are each independently selected from the group consisting of hydrogen and $C_1$-$C_4$alkyl wherein $R^a$ and $R^c$ may together form a $C_1$-$C_3$alkylene chain;
$R^1$ is selected from the group consisting of $C_1$-$C_6$alkyl-, $C_1$-$C_6$haloalkyl-, $C_1$-$C_6$alkoxy-$C_1$-$C_3$alkyl-, $C_1$-$C_6$haloalkoxy-$C_1$-$C_3$alkyl- and phenyl wherein the phenyl is optionally substituted by one or more (e.g one, two or three) substituents selected from the group consisting of halogen, $C_1$-$C_6$alkyl-, $C_1$-$C_6$alkoxy-, nitro and cyano;
$R^2$ is selected from the group consisting of $C_1$-$C_6$alkyl-, $C_1$-$C_6$ haloalkyl, $C_2$-$C_6$alkenyl-, $C_2$-$C_6$haloalkenyl-, $C_2$-$C_6$alkynyl-, $C_2$-$C_6$haloalkynyl-, $C_1$-$C_6$alkoxyC$_1$-$C_3$alkyl-, $C_1$-$C_6$haloalkoxyC$_1$-$C_3$alkyl-, $C_1$-$C_6$alkoxyC$_2$-$C_3$alkoxyC$_1$-$C_3$alkyl-, —(CH$_2$)$_n$—C$_3$-C$_6$cycloalkyl, benzyl, phenyl and a five or six-membered heteroaryl, the heteroaryl containing from one to three heteroatoms each independently selected from the group consisting of oxygen, nitrogen and sulphur, and wherein the benzyl, phenyl or heteroaryl may be optionally substituted by one or more substituents selected from the group consisting of halogen, $C_1$-$C_6$alkyl-, $C_2$-$C_6$alkenyl-, $C_2$-$C_6$alkynyl-, $C_1$-$C_6$haloalkyl-, $C_1$-$C_6$alkoxy-, $C_1$-$C_6$alkoxyC$_1$-$C_3$alkyl-, $C_1$-$C_6$alkoxyC$_1$-C$_3$alkoxy-, $C_1$-$C_6$haloalkoxy-, $C_1$-$C_6$alkyl-S(O)p-, cyano and nitro;
$R^3$ is selected from the group consisting of hydrogen, $C_1$-$C_4$ alkyl and $C_1$-$C_4$ haloalkyl;
n=1, 2 or 3; and
p=0, 1 or 2.

Alkyl groups having a chain length of from 1 to 6 carbon atoms include, for example, methyl (Me, CH$_3$), ethyl (Et, C$_2$H$_5$), n-propyl (n-Pr), isopropyl (i-Pr), n-butyl (n-Bu), isobutyl (i-Bu), sec-butyl and tert-butyl (t-Bu).

Alkenyl groups having a chain length of from 2 to 6 carbon atoms include, for example, —CH═CH$_2$ (vinyl) and —CH$_2$—CH═CH$_2$ (allyl).

Alkynyl groups having a chain length of from 2 to 6 carbon atoms include, for example, —C≡CH (ethynyl) and —CH$_2$—C≡CH (propargyl).

Halogen (or halo) encompasses fluorine, chlorine, bromine or iodine. The same correspondingly applies to halogen in the context of other definitions, such as haloalkyl, halkoalkenyl, haloalkynyl or halophenyl.

Haloalkyl groups having a chain length of from 1 to 6 carbon atoms are, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl, heptafluoro-n-propyl and perfluoro-n-hexyl.

Alkoxy groups preferably have a chain length of from 1 to 6 carbon atoms. Alkoxy is, for example, methoxy, ethoxy, propoxy, isopropoxy, n-butoxy, isobutoxy, sec-butoxy or tert-butoxy or a pentyloxy or hexyloxy isomer, preferably methoxy and ethoxy. It should also be appreciated that two alkoxy substituents present on the same carbon atom may be joined to form a spiro group. Thus, the methyl groups present in two methoxy substituents may be joined to form a spiro 1,3 dioxolane substituent, for example. Such a possibility is within the scope of the present invention.

Alkoxyalkyl groups preferably have from 1 to 6 carbon atoms. Alkoxyalkyl is, for example, methoxymethyl, methoxyethyl, ethoxymethyl, ethoxyethyl, n-propoxymethyl, n-propoxyethyl, isopropoxymethyl or isopropoxyethyl.

Haloalkoxy is, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy or 2,2,2-trichloroethoxy, preferably difluoromethoxy, 2-chloroethoxy or trifluoromethoxy.

$C_1$-$C_6$alkyl-S— (alkylthio) is, for example, methylthio, ethylthio, propylthio, isopropylthio, n-butylthio, isobutylthio, sec-butylthio or tert-butylthio, preferably methylthio or ethylthio.

$C_1$-$C_6$alkyl-S(O)— (alkylsulfinyl) is, for example, methylsulfinyl, ethylsulfinyl, propylsulfinyl, isopropylsulfinyl, n-butylsulfinyl, isobutylsulfinyl, sec-butylsulfinyl or tert-butylsulfinyl, preferably methylsulfinyl or ethylsulfinyl.

$C_1$-$C_6$alkyl-S(O)$_2$— (alkylsulfonyl) is, for example, methylsulfonyl, ethylsulfonyl, propylsulfonyl, isopropylsulfonyl, n-butylsulfonyl, isobutylsulfonyl, sec-butylsulfonyl or tert-butylsulfonyl, preferably methylsulfonyl or ethylsulfonyl.

$C_1$-$C_6$alkoxy-$C_1$-$C_3$alkyl- is, for example, methoxymethyl, methoxyethyl, ethoxymethyl, ethoxyethyl, n-propoxymethyl, n-propoxyethyl, isopropoxymethyl or isopropoxyethyl.

$C_1$-$C_6$haloalkoxy-$C_1$-$C_3$alkyl- is, for example, 2,2,2-trifluoroethoxymethyl-.

$C_1$-$C_6$alkoxy$C_2$-$C_3$alkoxy$C_1$-$C_3$alkyl- is, for example, methoxyethoxymethyl- Cycloalkyl groups preferably have from 3 to 6 ring carbon atoms, for example cyclopropyl (c-propyl (c-Pr)), cyclobutyl (c-butyl (c-Bu)), cyclopentyl (c-pentyl) and cyclohexyl (c-hexyl) and may be substituted or unsubstituted.

Heteroaryl is, for example, furanyl, thiophenyl, thiazolyl, oxazolyl, isoxazolyl, thiazolyl, pyrazolyl, isothiazolyl, pyridyl, pyridazinyl, pyrazinyl, pyrimidinyl and triazolyl.

In a particular aspect of the present invention there is provided a compound of Formula (I), wherein Q is Q1, $A^1$ is CH and $A^2$ is N.

In another aspect of the present invention there is provided a compound of Formula (I), wherein Q is Q1, $A^1$ is N and $A^2$ is CH.

In a preferred embodiment, Q is Q1 and $R^1$ is selected from the group consisting of methyl, ethyl and propyl, preferably methyl.

Particularly preferred is a compound of Formula (I) wherein Q is Q1 and both $A^1$ and $A^2$ are N.

In another particular aspect of the present invention there is provided a compound of Formula (I), wherein Q is Q2 and $X^1$ is $CR^eR^f$.

In another aspect of the present invention there is provided a compound of Formula (I), wherein Q is Q2, $X^1$ is $CR^eR^f$ and $R^a$, $R^b$, $R^c$, $R^d$, $R^e$ and $R^f$ are hydrogen.

In another aspect of the present invention there is provided a compound of Formula (I), wherein Q is Q2, $X^1$ is $CR^eR^f$ and $R^b$, $R^d$, $R^e$ and $R^f$ are hydrogen and $R^a$ and $R^c$ together form a $C_2$alkylene (i.e —$CH_2$—$CH_2$—) chain.

In one particular aspect, $R^2$ is selected from the group consisting of $C_1$-$C_6$ alkyl (e.g methyl, ethyl, n-propyl, n-butyl, i-pentyl) and $C_1$-$C_6$haloalkyl (e.g 1,1,1 trifluorobutyl-).

In another aspect $R^2$ is phenyl or a heteroaryl selected from the group consisting of furanyl, thiophenyl, thiazolyl, oxazolyl, isoxazolyl, thiazolyl, pyrazolyl, isothiazolyl, pyridyl, pyridazinyl, pyrazinyl, pyrimidinyl and triazolyl all of which may be optionally substituted as described herein. In a preferred embodiment, $R^2$ is phenyl which may be optionally substituted as described herein. In a particularly preferred embodiment, $R^2$ is phenyl optionally substituted by one or more (e.g one, two or three) substituents selected from the group consisting of halogen (especially fluorine and/or chlorine), $C_1$-$C_6$alkyl- (especially methyl), $C_1$-$C_6$haloalkyl- (especially trifluoromethyl), $C_1$-$C_6$alkoxy- (especially methoxy-), $C_1$-$C_6$haloalkoxy- (especially trifluoromethoxy-, $C_1$-$C_6$alkyl-S(O)p- (especially —$SO_2$-methyl), cyano and nitro.

In a preferred embodiment $R^3$ is hydrogen.

Compounds of Formula (I) (and certain intermediate compounds used to synthesise compound of Formula (I)) may contain asymmetric centres and may be present as a single enantiomer, pairs of enantiomers in any proportion or, where more than one asymmetric centre are present, contain diastereoisomers in all possible ratios. Typically one of the enantiomers has enhanced biological activity compared to the other possibilities.

Similarly, where there are disubstituted alkenes, these may be present in E or Z form or as mixtures of both in any proportion.

Furthermore, compounds of Formula (I) may be in equilibrium with alternative tautomeric forms. It should be appreciated that all tautomeric forms (single tautomer or mixtures thereof), racemic mixtures and single isomers are included within the scope of the present invention.

The present invention also includes agronomically acceptable salts that the compounds of Formula (I) may form with amines (for example ammonia, dimethylamine and triethylamine), alkali metal and alkaline earth metal bases or quaternary ammonium bases. Among the alkali metal and alkaline earth metal hydroxides, oxides, alkoxides and hydrogen carbonates and carbonates used as salt formers, emphasis is to be given to the hydroxides, alkoxides, oxides and carbonates of lithium, sodium, potassium, magnesium and calcium, but especially those of sodium, magnesium and calcium. The corresponding trimethylsulfonium salt may also be used.

The compounds of Formula (I) according to the invention can be used as herbicides by themselves, but they are generally formulated into herbicidal compositions using formulation adjuvants, such as carriers, solvents and surface-active agents (SFAs). Thus, the present invention further provides a herbicidal composition comprising a herbicidal compound according to any one of the previous claims and an agriculturally acceptable formulation adjuvant. The composition can be in the form of concentrates which are diluted prior to use, although ready-to-use compositions can also be made. The final dilution is usually made with water, but can be made instead of, or in addition to, water, with, for example, liquid fertilisers, micronutrients, biological organisms, oil or solvents.

The herbicidal compositions generally comprise from 0.1 to 99% by weight, especially from 0.1 to 95% by weight, compounds of Formula I and from 1 to 99.9% by weight of a formulation adjuvant which preferably includes from 0 to 25% by weight of a surface-active substance.

The compositions can be chosen from a number of formulation types, many of which are known from the Manual on Development and Use of FAO Specifications for Plant Protection Products, 5th Edition, 1999. These include dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), micro-emulsions (ME), suspension concentrates (SC), aerosols, capsule suspensions (CS) and seed treatment formulations. The formulation type chosen in any instance will depend upon the particular purpose envisaged and the physical, chemical and biological properties of the compound of Formula (I).

Dustable powders (DP) may be prepared by mixing a compound of Formula (I) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulphur, lime, flours, talc and other organic and inorganic solid carriers) and mechanically grinding the mixture to a fine powder.

Soluble powders (SP) may be prepared by mixing a compound of Formula (I) with one or more water-soluble inorganic salts (such as sodium bicarbonate, sodium carbonate or magnesium sulphate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of Formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of Formula (I) and one or more powdered solid diluents or carriers, or from preformed blank granules by absorbing a compound of Formula (I) (or a solution thereof, in a suitable agent) in a porous granular material (such as pumice, attapulgite clays, fuller's earth, kieselguhr, diatomaceous earths or ground corn cobs) or by adsorbing a compound of Formula (I) (or a solution thereof, in a suitable agent) on to a hard core material (such as sands, silicates, mineral carbonates, sulphates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of Formula (I) in water or an organic solvent, such as a ketone, alcohol or glycol ether. These solutions may contain a surface active agent (for example to improve water dilution or prevent crystallisation in a spray tank).

Emulsifiable concentrates (EC) or oil-in-water emulsions (EW) may be prepared by dissolving a compound of Formula (I) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment.

Preparation of an EW involves obtaining a compound of Formula (I) either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of Formula (I) is present initially in either the water or the solvent/SFA blend. Suitable solvents for use in MEs include those hereinbefore described for use in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of Formula (I). SCs may be prepared by ball or bead milling the solid compound of Formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of Formula (I) may be dry milled and added to water, containing agents hereinbefore described, to produce the desired end product.

Aerosol formulations comprise a compound of Formula (I) and a suitable propellant (for example n-butane). A compound of Formula (I) may also be dissolved or dispersed in a suitable medium (for example water or a water miscible liquid, such as n-propanol) to provide compositions for use in non-pressurised, hand-actuated spray pumps.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains a compound of Formula (I) and, optionally, a carrier or diluent therefor. The polymeric shell may be produced by either an interfacial polycondensation reaction or by a coacervation procedure. The compositions may provide for controlled release of the compound of Formula (I) and they may be used for seed treatment. A compound of Formula (I) may also be formulated in a biodegradable polymeric matrix to provide a slow, controlled release of the compound.

The composition may include one or more additives to improve the biological performance of the composition, for example by improving wetting, retention or distribution on surfaces; resistance to rain on treated surfaces; or uptake or mobility of a compound of Formula (I). Such additives include surface active agents (SFAs), spray additives based on oils, for example certain mineral oils or natural plant oils (such as soy bean and rape seed oil), and blends of these with other bio-enhancing adjuvants (ingredients which may aid or modify the action of a compound of Formula (I).

Wetting agents, dispersing agents and emulsifying agents may be SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulphuric acid (for example sodium lauryl sulphate), salts of sulphonated aromatic compounds (for example sodium dodecylbenzenesulphonate, calcium dodecylbenzenesulphonate, butylnaphthalene sulphonate and mixtures of sodium di-isopropyl- and tri-isopropyl-naphthalene sulphonates), ether sulphates, alcohol ether sulphates (for example sodium laureth-3-sulphate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulphosuccinamates, paraffin or olefine sulphonates, taurates and lignosulphonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

The composition of the present may further comprise at least one additional pesticide. For example, the compounds according to the invention can also be used in combination with other herbicides or plant growth regulators. In a preferred embodiment the additional pesticide is a herbicide and/or herbicide safener. Examples of such mixtures are (in which 'I' represents a compound of Formula I). I+acetochlor, I+acifluorfen, I+acifluorfen-sodium, I+aclonifen, I+acrolein, I+alachlor, I+alloxydim, I+ametryn, I+amicarbazone, I+amidosulfuron, I+aminopyralid, I+amitrole, I+anilofos, I+asulam, I+atrazine, I+azafenidin, I+azimsulfuron, I+BCPC, I+beflubutamid, I+benazolin, I+bencarbazone, I+benfluralin, I+benfuresate, I+bensulfuron, I+bensulfuron-methyl, I+bensulide, I+bentazone, I+benzfendizone, I+benzobicyclon, I+benzofenap, I+bicyclopyrone, I+bifenox, I+bilanafos, I+bispyribac, I+bispyribac-sodium, I+borax, I+bromacil, I+bromobutide, I+bromoxynil, I+butachlor, I+butamifos, I+butralin, I+butroxydim, I+butylate, I+cacodylic acid, I+calcium chlorate, I+cafenstrole, I+carbetamide, I+carfentrazone, I+carfentrazone-ethyl, I+chlorflurenol, I+chlorflurenol-methyl, I+chloridazon, I+chlorimuron, I+chlorimuron-ethyl, I+chloroacetic acid, I+chlorotoluron, I+chlorpropham, I+chlorsulfuron, I+chlorthal, I+chlorthal-dimethyl, I+cinidon-ethyl, I+cinmethylin, I+cinosulfuron, I+cisanilide, I+clethodim, I+clodinafop, I+clodinafop-propargyl, I+clomazone, I+clomeprop, I+clopyralid, I+cloransulam, I+cloransulam-methyl, I+cyanazine, I+cycloate, I+cyclosulfamuron, I+cycloxydim, I+cyhalofop, I+cyhalofop-butyl, I+2,4-D, I+daimuron, I+dalapon, I+dazomet, I+2,4-DB, I+I+desmedipham, I+dicamba, I+dichlobenil, I+dichlorprop, I+dichlorprop-P, I+diclofop, I+diclofopmethyl, I+diclosulam, I+difenzoquat, I+difenzoquat metilsulfate, I+diflufenican, I+diflufenzopyr, I+dimefuron, I+dimepiperate, I+dimethachlor, I+dimethametryn, I+dimethenamid, I+dimethenamid-P, I+dimethipin, I+dimethylarsinic acid, I+dinitramine, I+dinoterb, I+diphenamid, I+dipropetryn, I+diquat, I+diquat dibromide, I+dithiopyr, I+diuron, I+endothal, I+EPTC, I+esprocarb, I+ethalfluralin, I+ethametsulfuron, I+ethametsulfuron-methyl, I+ethephon, I+ethofumesate, I+ethoxyfen, I+ethoxysulfuron, I+etobenzanid, I+fenoxaprop-P, I+fenoxaprop-P-ethyl, I+fenquinotrione, I+fentrazamide, I+ferrous sulfate, I+flamprop-M, I+flazasulfuron, I+florasulam, I+fluazifop, I+fluazifop-butyl, I+fluazifop-P, I+fluazifop-P-butyl, I+fluazolate, I+flucarbazone, I+flucarbazone-sodium, I+flucetosulfuron, I+fluchloralin, I+flufenacet, I+flufenpyr, I+flufenpyr-ethyl, I+flumetralin, I+flumetsulam, I+flumiclorac, I+flumiclorac-pentyl, I+flumioxazin, I+flumipropin, I+fluometuron, I+fluoroglycofen, I+fluoroglycofen-ethyl, I+fluoxaprop, I+flupoxam, I+flupropacil, I+flupropanate, I+flupyrsulfuron, I+flupyrsulfuron-methyl-sodium, I+flurenol, I+fluridone, I+flurochloridone, I+fluroxypyr, I+flurtamone, I+fluthiacet, I+fluthiacet-methyl, I+fomesafen, I+foramsulfuron, I+fosamine, I+glufosinate, I+glufosinate-ammonium, I+glyphosate, I+halauxifen, I+halosulfuron, I+halosulfuron-methyl, I+haloxyfop, I+haloxyfop-P, I+hexazinone, I+imazamethabenz, I+imazamethabenz-methyl, I+imazamox, I+imazapic, I+imazapyr, I+imazaquin, I+imazethapyr, I+imazosulfuron, I+indanofan, I+indaziflam, I+iodomethane, I+iodosulfuron, I+iodosulfuron-methyl-sodium, I+ioxynil, I+isoproturon, I+isouron, I+isoxaben, I+isoxachlortole, I+isoxaflutole, I+isoxapyrifop, I+karbutilate, I+lactofen, I+lenacil, I+linuron, I+mecoprop, I+mecoprop-P, I+mefenacet, I+mefluidide, I+mesosulfuron, I+mesosulfuronmethyl, I+mesotrione, I+metam, I+metamifop, I+metamitron, I+metazachlor, I+methabenzthiazuron, I+methazole, I+methylarsonic acid, I+methyldymron, I+methyl isothiocyanate, I+metolachlor, I+S-metolachlor, I+metosulam, I+metoxuron, I+metribuzin, I+metsulfuron, I+metsulfuron-methyl, I+molinate, I+monolinuron, I+naproanilide, I+napropamide, I+naptalam, I+neburon, I+nicosulfuron, I+n-methyl glyphosate, I+nonanoic acid, I+norflurazon, I+oleic acid (fatty acids), I+orbencarb, I+orthosulfamuron, I+oryzalin, I+oxadiargyl, I+oxadiazon, I+oxasulfuron, I+oxaziclomefone, I+oxyfluorfen, I+paraquat, I+paraquat dichloride, I+pebulate, I+pendimethalin, I+penoxsulam, I+pentachlorophenol, I+pentanochlor, I+pentoxazone, I+pethoxamid, I+phenmedipham, I+picloram, I+picolinafen, I+pinoxaden, I+piperophos, I+pretilachlor, I+primisulfuron, I+primisulfuron-methyl, I+prodiamine, I+profoxydim, I+prohexadione-calcium, I+prometon, I+prometryn, I+propachlor, I+propanil, I+propaquizafop, I+propazine, I+propham, I+propisochlor, I+propoxycarbazone, I+propoxycarbazone-sodium, I+propyzamide, I+prosulfocarb, I+prosulfuron, I+pyraclonil, I+pyraflufen, I+pyraflufen-ethyl, I+pyrasulfotole, I+pyrazolynate, I+pyrazosulfuron, I+pyrazosulfuron-ethyl, I+pyrazoxyfen, I+pyribenzoxim, I+pyributicarb, I+pyridafol, I+pyridate, I+pyriftalid, I+pyriminobac, I+pyriminobac-methyl, I+pyrimisulfan, I+pyrithiobac, I+pyrithiobac-sodium, I+pyroxasulfone, I+pyroxsulam, I+quinclorac, I+quinmerac, I+quinoclamine, I+quizalofop, I+quizalofop-P, I+rimsulfuron, I+saflufenacil, I+sethoxydim, I+siduron, I+simazine, I+simetryn, I+sodium chlorate, I+sulcotrione, I+sulfentrazone, I+sulfometuron, I+sulfometuron-methyl, I+sulfosate, I+sulfosulfuron, I+sulfuric acid, I+tebuthiuron, I+tefuryltrione, I+tembotrione, I+tepraloxydim, I+terbacil, I+terbumeton, I+terbuthylazine, I+terbutryn, I+thenylchlor, I+thiazopyr, I+thifensulfuron, I+thiencarbazone, I+thifensulfuron-methyl, I+thiobencarb, I+topramezone, I+tralkoxydim, I+tri-allate, I+triasulfuron, I+triaziflam, I+tribenuron, I+tribenuron-methyl, I+triclopyr, I+trietazine, I+trifloxysulfuron, I+trifloxysulfuron-sodium, I+trifluralin, I+triflusulfuron, I+triflusulfuron-methyl, I+trihydroxytriazine, I+trinexapac-ethyl, I+tritosulfuron, I+[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester (CAS RN 353292-31-6). The compounds of the present invention may also be combined with herbicidal compounds disclosed in WO06/024820 and/or WO07/096576.

The mixing partners of the compound of Formula I may also be in the form of esters or salts, as mentioned e.g. in The Pesticide Manual, Sixteenth Edition, British Crop Protection Council, 2012.

The compound of Formula I can also be used in mixtures with other agrochemicals such as fungicides, nematicides or insecticides, examples of which are given in The Pesticide Manual.

The mixing ratio of the compound of Formula I to the mixing partner is preferably from 1:100 to 1000:1.

The mixtures can advantageously be used in the above-mentioned formulations (in which case "active ingredient" relates to the respective mixture of compound of Formula I with the mixing partner).

The compounds of Formula I according to the invention can also be used in combination with one or more safeners. Likewise, mixtures of a compound of Formula I according to the invention with one or more further herbicides can also be used in combination with one or more safeners. The safeners can be AD 67 (MON 4660), benoxacor, cloquintocet-mexyl, cyprosulfamide (CAS RN 221667-31-8), dichlormid, fenchlorazole-ethyl, fenclorim, fluxofenim, furilazole and the corresponding R isomer, isoxadifen-ethyl, mefenpyr-diethyl, oxabetrinil, N-isopropyl-4-(2-methoxy-benzoylsulfamoyl)-benzamide (CAS RN 221668-34-4). Other possibilities include safener compounds disclosed in, for example, EP0365484 e.g N-(2-methoxybenzoyl)-4-[(methylaminocarbonyl)amino]benzenesulfonamide. Particularly preferred are mixtures of a compound of Formula I with cyprosulfamide, isoxadifen-ethyl, cloquintocet-mexyl and/or N-(2-methoxybenzoyl)-4-[(methylaminocarbonyl)amino]benzenesulfonamide.

The safeners of the compound of Formula I may also be in the form of esters or salts, as mentioned e.g. in The Pesticide Manual, 16$^{th}$ Edition (BCPC), 2012. The reference to cloquintocet-mexyl also applies to a lithium, sodium, potassium, calcium, magnesium, aluminium, iron, ammonium, quaternary ammonium, sulfonium or phosphonium salt thereof as disclosed in WO 02/34048, and the reference to fenchlorazole-ethyl also applies to fenchlorazole, etc.

Preferably the mixing ratio of compound of Formula I to safener is from 100:1 to 1:10, especially from 20:1 to 1:1.

The mixtures can advantageously be used in the above-mentioned formulations (in which case "active ingredient" relates to the respective mixture of compound of Formula I with the safener).

The present invention still further provides a method of controlling weeds at a locus said method comprising application to the locus of a weed controlling amount of a composition comprising a compound of Formula (I). Moreover, the present invention further provides a method of selectively controlling weeds at a locus comprising crop plants and weeds, wherein the method comprises application to the locus of a weed controlling amount of a composition according to the present invention. 'Controlling' means killing, reducing or retarding growth or preventing or reducing germination. Generally the plants to be controlled are unwanted plants (weeds). 'Locus' means the area in which the plants are growing or will grow. Some crop plants may be inherently tolerant to herbicidal effects of compounds of Formula (I). However, in some instances tolerance may need to be engineered into the crop plant, for example by way of genetic engineering. Thus, it is possible that the crop plant is rendered tolerant to HPPD-inhibitors via genetic engineering. Methods of rending crop plants tolerant to HPPD-inhibitors are known, for example from WO0246387. Thus in an even more preferred embodiment the crop plant is transgenic in respect of a polynucleotide comprising a DNA sequence which encodes an HPPD-inhibitor resistant HPPD enzyme derived from a bacterium, more particularly from *Pseudomonas fluorescens* or *Shewanella colwelliana*, or from a plant, more particularly, derived from a monocot plant or, yet more particularly, from a barley, maize, wheat, rice, *Brachiaria, Cenchrus, Lolium, Festuca, Setaria, Eleusine, Sorghum* or *Avena* species. Several HPPD-tolerant soybean transgenic "events" are known, and include for example SYHT04R (WO2012/082542), SYHT0H2 (WO2012/082548) and FG72. Crop plants in which the composition according to the invention can be used thus include crops such as cereals, for example barley and wheat, cotton, oilseed rape, sunflower, maize, rice, soybeans, sugar beet, sugar cane and turf.

Crop plants can also include trees, such as fruit trees, palm trees, coconut trees or other nuts. Also included are vines such as grapes, fruit bushes, fruit plants and vegetables.

The rates of application of compounds of Formula I may vary within wide limits and depend on the nature of the soil, the method of application (pre- or post-emergence; seed dressing; application to the seed furrow; no tillage application etc.), the crop plant, the weed(s) to be controlled, the prevailing climatic conditions, and other factors governed by the method of application, the time of application and the target crop. The compounds of Formula I according to the invention are generally applied at a rate of from 10 to 2000 g/ha, especially from 50 to 1000 g/ha.

The application is generally made by spraying the composition, typically by tractor mounted sprayer for large areas, but other methods such as dusting (for powders), drip or drench can also be used.

Crop plants are to be understood as also including those crop plants which have been rendered tolerant to herbicides or classes of herbicides (e.g. ALS-, GS-, EPSPS-, PPO-, ACCase- and HPPD-inhibitors) by conventional methods of breeding or by genetic engineering. An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®.

Crop plants are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). The Bt toxin is a protein that is formed naturally by *Bacillus thuringiensis* soil bacteria. Examples of toxins, or transgenic plants able to synthesise such toxins, are described in EP-A-451 878, EP-A-374 753, WO 93/07278, WO 95/34656, WO 03/052073 and EP-A-427 529. Examples of transgenic plants comprising one or more genes that code for an insecticidal resistance and express one or more toxins are KnockOut® (maize), Yield Gard® (maize), NuCOTN33B® (cotton), Bollgard® (cotton), NewLeaf® (potatoes), NatureGard® and Protexcta®. Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Crop plants are also to be understood to include those which are obtained by conventional methods of breeding or genetic engineering and contain so-called output traits (e.g. improved storage stability, higher nutritional value and improved flavour).

Other useful plants include turf grass for example in golf-courses, lawns, parks and roadsides, or grown commercially for sod, and ornamental plants such as flowers or bushes.

The compositions can be used to control unwanted plants (collectively, 'weeds'). The weeds to be controlled may be both monocotyledonous species, for example *Agrostis, Alopecurus, Avena, Brachiaria, Bromus, Cenchrus, Cyperus, Digitaria, Echinochloa, Eleusine, Lolium, Monochoria, Rottboellia, Sagittaria, Scirpus, Setaria* and *Sorghum*, and dicotyledonous species, for example *Abutilon, Amaranthus, Ambrosia, Chenopodium, Chrysanthemum, Conyza, Galium, Ipomoea, Nasturtium, Sida, Sinapis, Solanum, Stellaria, Veronica, Viola* and *Xanthium*. Weeds can also include plants which may be considered crop plants but which are growing outside a crop area ('escapes'), or which grow from seed left over from a previous planting of a different crop ('volunteers'). Such volunteers or escapes may be tolerant to certain other herbicides.

The compounds of the present invention can be prepared according to the following schemes.

Scheme 1:- Reaction of an activated carboxylic acid with a 5-aminotetrazole or an aminotriazole:

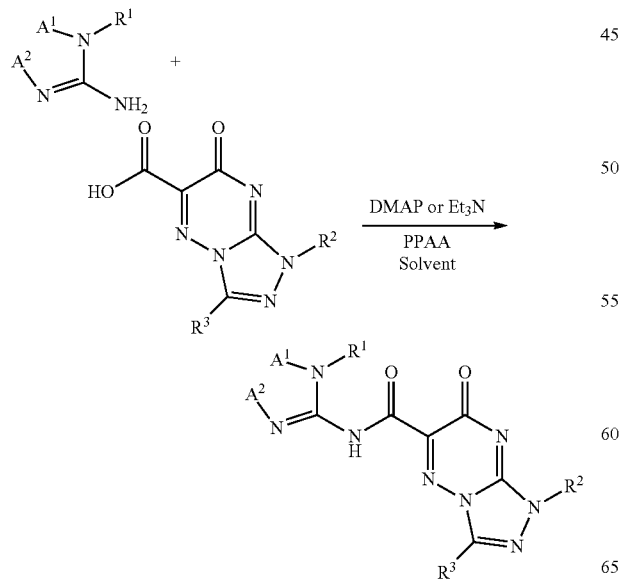

Scheme 2:- Reaction of an activated carboxylic acid with a 5-(alkylamino)tetrazole:

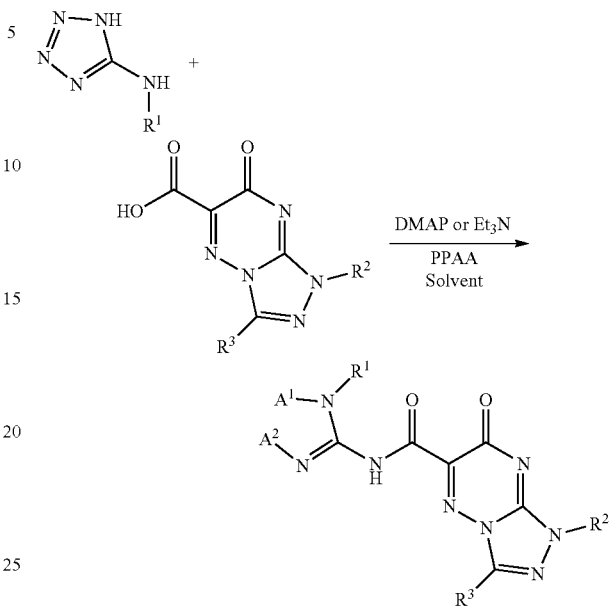

In each case, DMAP=4-(dimethylamino) pyridine, $Et_3N$=triethylamine, PPAA=1-propanephosphonic acid cyclic anhydride, the solvent is a non-protic organic solvent such as ethyl acetate, tetrahydofuran, 1,4-dioxane, dimethylformamide or dichloromethane, and the reaction may be subjected to heating by microwave irradiation.

Scheme 3: Reaction of an acid chloride with an aminotriazole or an aminotetrazole:

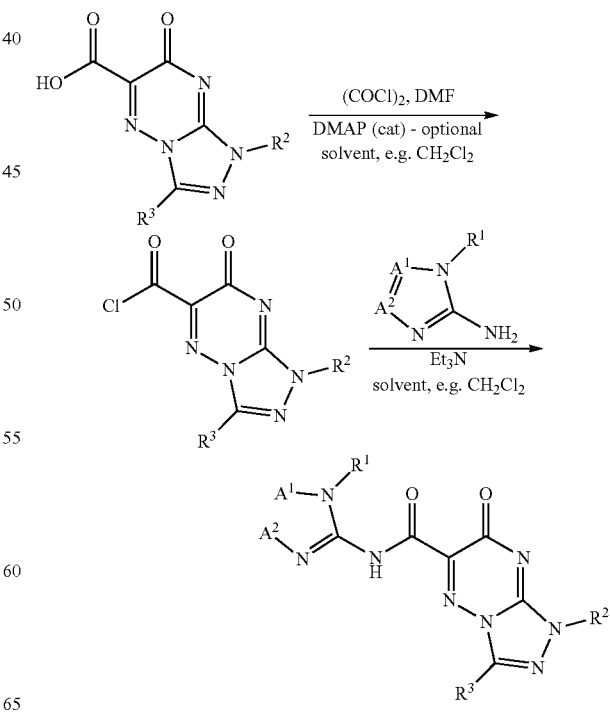

where DMF=dimethylformamide.

Scheme 4: Activation of an acid with N,N'-carbonyldiimidazole (CDI), and reaction with an aminotriazole or an aminotetrazole:

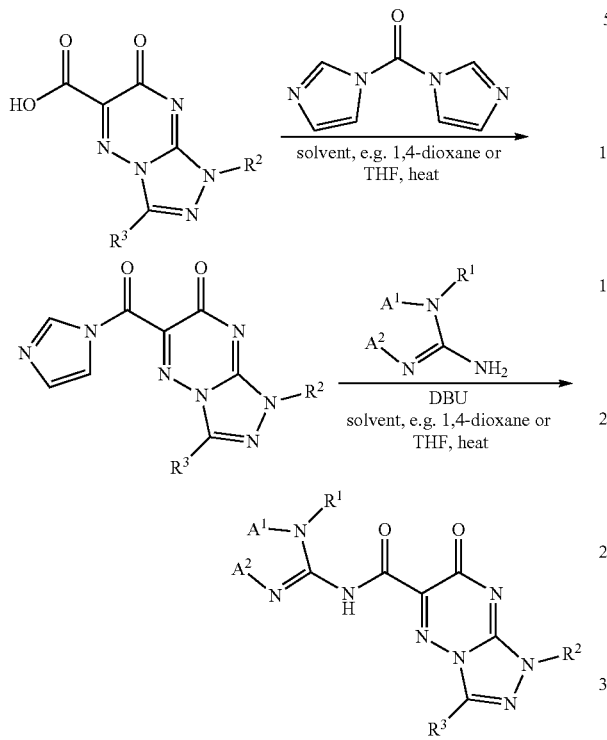

where THF=tetrahydrofuran and DBU=1,8-diazabicyclo[5.4.0]undec-7-ene

Scheme 5: Reaction of a carboxylic ester with an aminotriazole or an aminotetrazole:

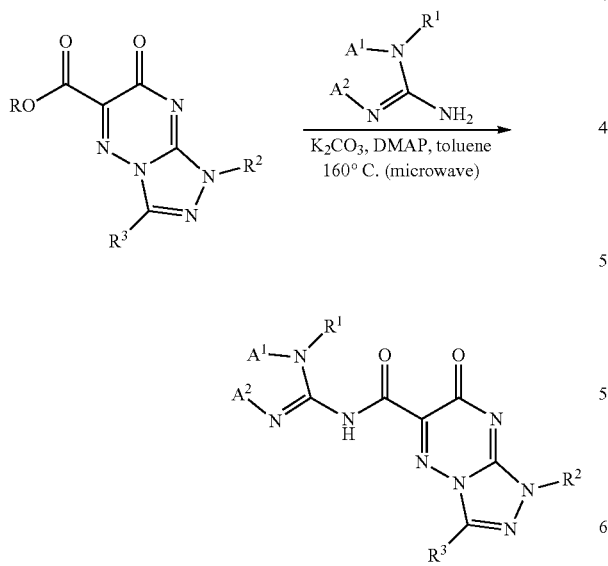

The carboxylic acids and esters utilised in Schemes 1-5 can be prepared by known methods, or methods analogous to known methods. Examples of such methods are given in Schemes 6 and 7, below.

Scheme 6: Preparation of N-aryl and N-heteroaryl triazolotriazinone carboxylic esters and acids:

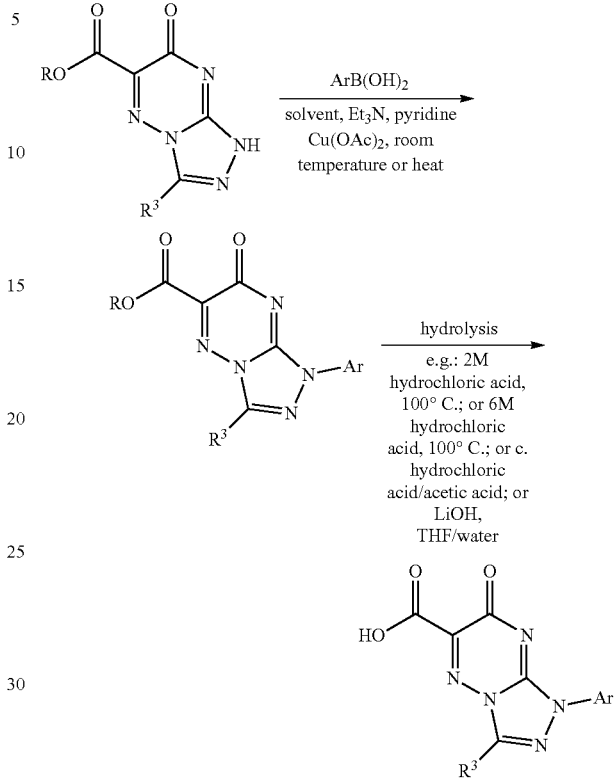

where Ar is an optionally substituted aryl- or heteroaryl group, and the solvent is a non-protic organic solvent such as tetrahydrofuran or dichloromethane.

Scheme 7: Preparation of N-aryl triazolotriazinone carboxylic esters and acids:

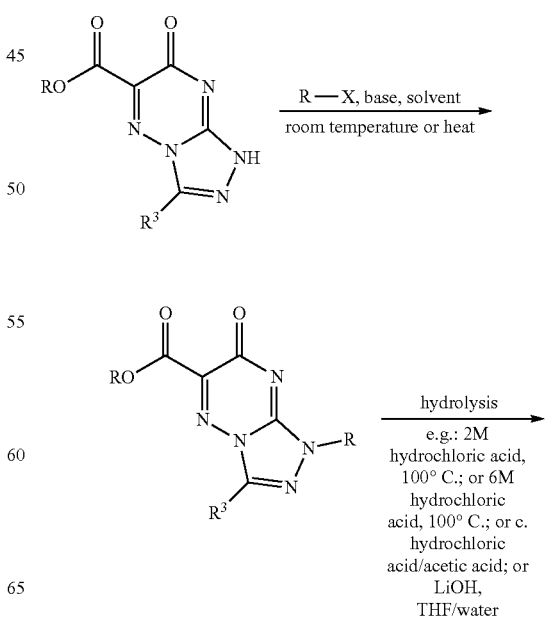

-continued

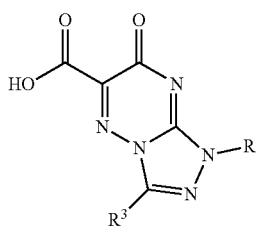

where R is an optionally substituted alkyl group, X is a leaving group such as chloro, bromo, iodo, 4-toluenesulfonyloxy or trifluoromethanesulfonyloxy, solvent is a non-protic organic solvent such as dimethylformamide (DMF) or acetonitrile and the base is an inorganic base such as caesium carbonate, potassium carbonate or calcium carbonate.

The triazolotriazinone carboxylic esters utilised in Schemes 6 and 7 can be prepared by known methods, or methods analogous to known methods. An example of such a method is given in Scheme 8, below.

Scheme 8: Preparation of triazolotriazinone carboxylic esters:

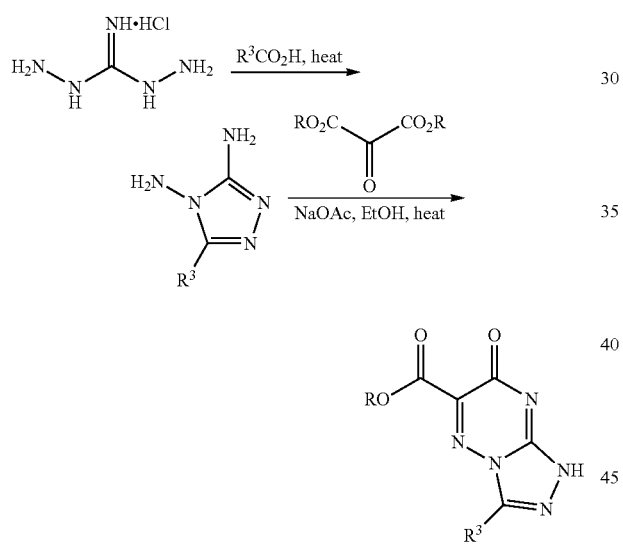

where NaOAc=sodium acetate and EtOH=ethanol.

Scheme 9: Acylation of a cyclic 1,3-dione:

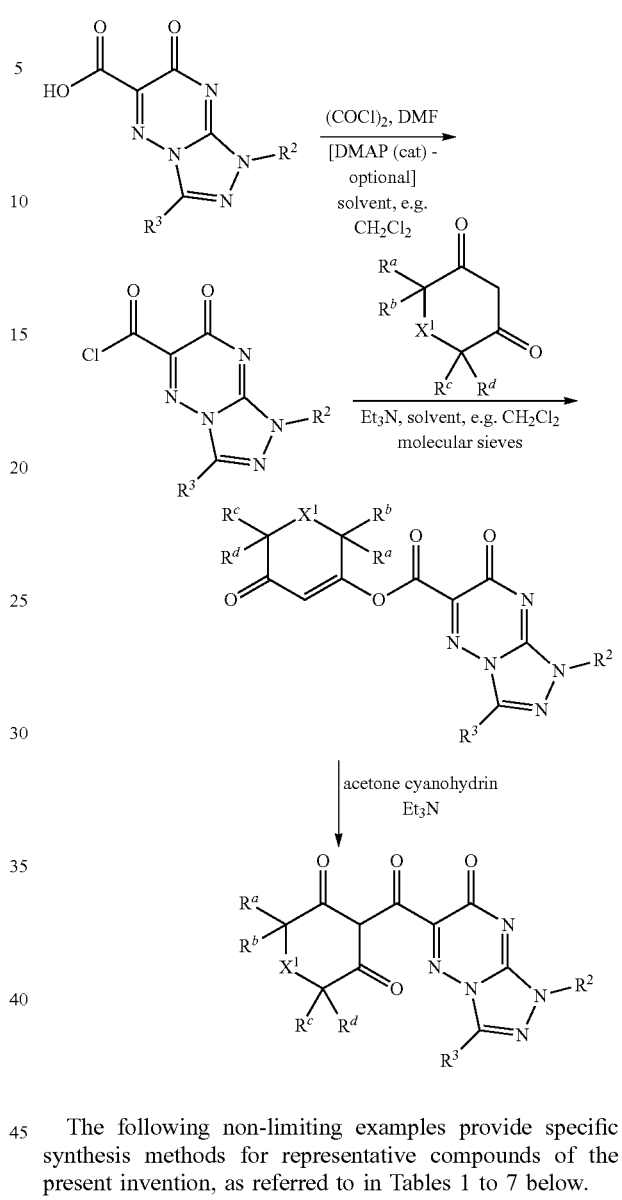

The following non-limiting examples provide specific synthesis methods for representative compounds of the present invention, as referred to in Tables 1 to 7 below.

PREPARATIVE EXAMPLE 1: PREPARATION OF COMPOUND 1.001

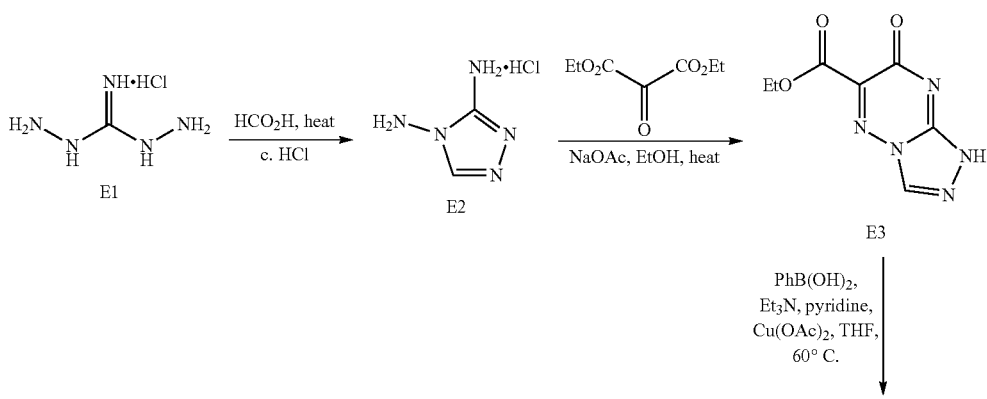

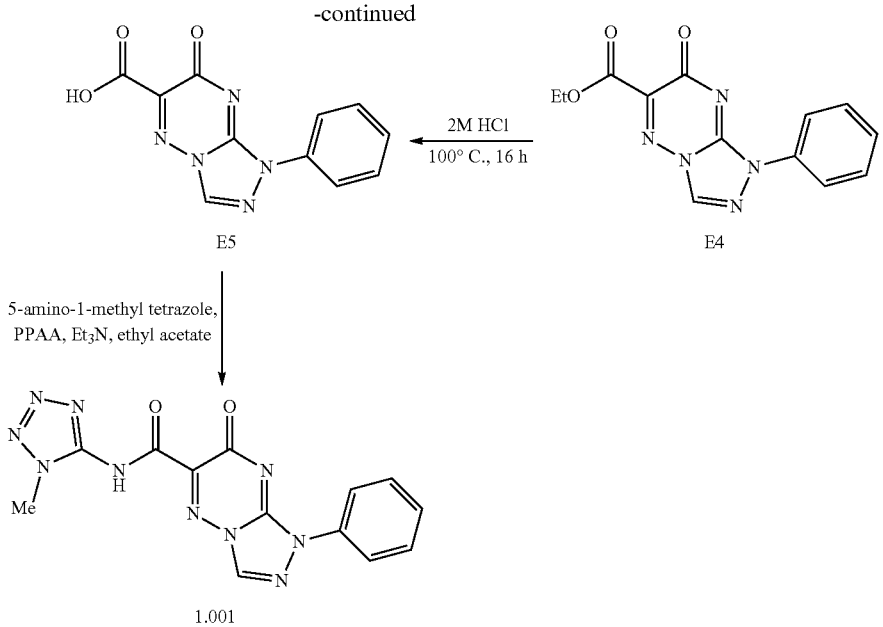

Step 1:

A solution of compound E1 (20.0 g, 0.162 mol) in formic acid (100 mL) was heated to 120° C. and stirred for 6 hours. The reaction mixture was then cooled to room temperature, and conc. HCl (100 mL) was added. The mixture was then heated to 120° C. and stirred for a further 6 hours. The cooled mixture was then concentrated under reduced pressure, and the residue was triturated with methanol followed by diethyl ether to afford compound E2 (20.0 g).

1H nmr (d6-DMSO): 6.18 (2H, br s); 8.29 (2H, br s); 8.43 (1H, s); 13.99 (1H, br s)

Step 2:

A stirred solution of compound E2 (20.0 g, 0.148 mol) in ethanol (200 ml) was treated with sodium acetate (20.0 g, 0.222 mol) followed by diethyl ketomalonate (45 mL, 0.296 mol). The reaction mixture was then heated to 90° C. and stirred for 16 hours. The cooled solution was then concentrated under reduced pressure to leave a yellow gummy solid, which was stirred with water (200 mL) for 30 min. The solid was then filtered off, washed with diethyl ether and dried under high vacuum to afford compound E3 (12.0 g).

1H nmr (d6-DMSO): 1.30 (3H, t); 4.36 (2H, q); 9.13 (1H, s); 14.23 (1H, br s)

Step 3:

A stirred solution of compound E3 (5.0 g, 23.9 mmol) and phenylboronic acid (5.8 g, 47.8 mmol) in tetrahydrofuran (THF; 200 mL) was treated with triethylamine (10.0 mL, 71.7 mmol), pyridine (6 mL, 71.7 mmol) and copper (II) acetate (8.6 g, 47.8 mmol). The reaction mixture was heated to 60° C. and stirred for 4 hours. The cooled mixture was then filtered, the solid material was washed twice with dichloromethane and the combined filtrates were evaporated under reduced pressure. The residue was dissolved in ethyl acetate and the organic layer was washed with aqueous 2M HCl followed by brine. The organic layer was then separated, dried over anhydrous sodium sulphate, filtered and evaporated under reduced pressure to obtain the crude product. This was purified by silica-gel chromatography, eluting with 10-50% ethyl acetate-hexane mixtures, to afford compound E4 (1.2 g).

1H nmr (d6-DMSO): 1.32 (3H, t); 4.40 (2H, q); 7.45 (1H, t); 7.61 (2H, t); 7.98 (2H, d); 9.48 (1H, s)

Step 4:

A mixture of compound E4 (0.50 g, 1.75 mmol) and 2M hydrochloric acid (10 mL) was stirred at 100° C. for 16 hours. After completion of the reaction, the cooled reaction mixture was concentrated under reduced pressure, and the residue was triturated with methanol and diethyl ether to afford compound E5 (0.41 g).

Step 5:

A stirred solution of compound E5 (0.30 g, 1.16 mmol) in THF (30 mL) was treated with 5-amino-1-methyltetrazole (0.12 g, 1.16 mmol), triethylamine (0.7 mL, 4.66 mmol), 1-propanephosphonic acid cyclic anhydride (PPAA) [50% in ethyl acetate (4 mL, 7 mmol)], and the mixture was stirred at room temperature for 16 hours. The reaction mixture was then diluted with ethyl acetate and the organic layer was washed with water, followed by brine. The organic layer was then separated, dried over anhydrous sodium sulphate, and evaporated under reduced pressure. The crude residue was purified by silica-gel chromatography, eluting with 0-10% methanol in dichloromethane, to obtain compound 1.001 (0.08 g).

1H nmr (d6-DMSO): 3.98 (3H, s); 7.48 (1H, t); 7.64 (2H, t); 8.01 (2H, d); 9.67 (1H, s); 12.34 (1H, br s)

PREPARATIVE EXAMPLE 2: PREPARATION OF COMPOUND 4.001

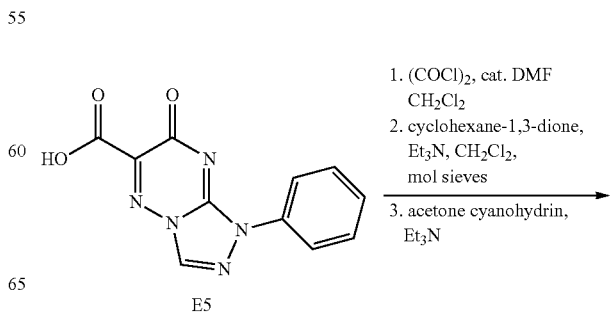

19
-continued

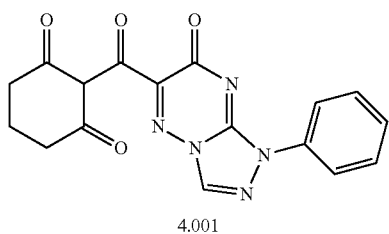

4.001

Step 1:

A stirred solution of compound E5, prepared as described in Preparative Example 1, Step 4, (0.30 g, 1.16 mmol) in dichloromethane (15 mL) was cooled to 0° C. and treated with dimethyl formamide (0.1 mL) followed by oxalyl chloride (0.3 mL, 2.41 mmol). The mixture was then allowed to warm to room temperature and stirred for 16 hours. The reaction mixture was then concentrated under reduced pressure and the residual crude acid chloride was dissolved in dichloromethane (15 mL) followed by the addition of molecular sieves. The reaction mixture was then cooled to 0° C. with stirring, and triethylamine (0.5 mL, 3.62 mmol) and cyclohexane-1,3-dione (0.16 g, 1.44 mmol) were added. The resulting mixture was allowed to warm to room temperature, and was stirred for a further 2 hours. Triethylamine (0.5 mL, 3.62 mmol) and acetone cyanohydrin (0.1 g, 1.2 mmol) were then added, and the reaction mixture was stirred at room temperature for 16 hours. The mixture was then diluted with dichloromethane and filtered through celite to remove the molecular sieves. The filtrate was washed with 1N HCl and brine, and the organic layer was separated, dried over anhydrous sodium sulfate, filtered and evaporated under reduced pressure to afford the crude product, which was purified by silica-gel chromatography (eluting with 1:4:4:8:20 mixture of water/ethanol/triethylamine/1,4-dioxane/toluene) to afford compound 4.001 (0.1 g).

1H nmr (d6-DMSO): 1.93-1.96 (2H, m); 2.33-2.60 (4H, m); 7.45 (1H, t); 7.61 (2H, t); 7.80 (2H, d); 9.42 (1H, s)

PREPARATIVE EXAMPLE 3: PREPARATION OF COMPOUND 1.028

Step 1:

By a method analogous to that described in Preparative Example 1, Step 3, but using compound E3 (1.324 g, 6.330 mmol), 2-methylphenylboronic acid (1.723 g, 12.67 mmol), powdered molecular sieves (4 A), pyridine (2.10 mL), copper (II) acetate (2.336 g, 12.72 mmol), a mixture of ethyl acetate (100 mL) and dichloromethane (100 mL) as solvent, and conducting the reaction at room temperature for 68 hours, compound E6 (0.165 g) was obtained as a white solid.

1Hnmr (CDCl$_3$): 8.43 (s, 1H), 7.46-7.42 (m, 1H), 7.40-7.33 (m, 3H), 4.51 (q, 2H), 2.27 (s, 3H), 1.44 (t, 3H)

Step 2:

A stirred solution of compound E6 (165 mg, 0.5513 mmol) in acetic acid (4 mL) was treated with conc. hydrochloric acid (1 mL), and the mixture was heated to 70° C. for 2 hours, then cooled to room temperature and allowed to stand overnight. The mixture was evaporated to dryness under reduced pressure, using toluene to azeotrope out remaining water, to afford compound E7 as an off white solid (133 mg).

1Hnmr (d6-DMSO): 9.49 (s, 1H), 7.52-7.38 (m, 4H), 2.23 (s, 3H)

Step 3:

By a method analogous to that described in Preparative Example 1, Step 5, but using compound E7 (133 mg, 0.4904 mmol), 5-amino-1-n-propyltetrazole (62 mg, 0.4876 mmol), 1-propanephosphonic acid cyclic anhydride (PPAA) [(50% in ethyl acetate (0.62 mL, 1.0 mmol), 4-(N,N-dimethylamino)pyridine (DMAP: 120 mg, 0.9528 mmol) and dichloromethane (10.0 mL) as solvent, compound 1.028 was obtained (154 mg).

1Hnmr (d6-DMSO): 12.27 (broad s, 1H), 9.65 (s, 1H), 7.55-7.40 (m, 4H), 4.29 (t, 2H), 2.24 (s, 3H), 1.92-1.80 (m, 2H), 0.87 (t, 3H)

PREPARATIVE EXAMPLE 4: PREPARATION OF COMPOUND 1.011

Step 1:

A stirred solution of compound E3 (2.0 g, 9.57 mmol) in acetonitrile (40 mL) was treated with potassium carbonate (2.6 g, 19.14 mmol) followed by 1,1,1-trifluoro-4-iodobutane (7.3 mL, 57.35 mmol). The reaction mixture was heated to 60° C. for 16 h, then cooled and concentrated to dryness under reduced pressure. The residue was purified by column chromatography on silica-gel, eluting with ethyl acetate/hexanes (50-100%) to obtain compound E8 (0.30 g).

1Hnmr (d6-DMSO): 9.24 (s, 1H), 4.37 (q, 2H), 4.14 (t, 2H), 2.34 (m, 2H), 1.99 (m, 2H), 1.30 (t, sH)

Step 2:

A stirred solution of compound E8 (300 mg, 0.39 mmol) in tetrahydrofuran (10 mL) was treated with a solution of lithium hydroxide monohydrate (0.078 g, 1.878 mmol) in water (5 mL), and the mixture was stirred at room temperature for 16 h. The solution was then concentrated a little under reduced pressure, the pH of the mixture was then adjusted to 2 with 1M hydrochloric acid, and this mixture was then evaporated to dryness under reduced pressure to afford crude compound E9 (200 mg), which was used in the next step without further purification.

1Hnmr (d6-DMSO): 9.27 (broad s, 1H), 4.16 (m, 2H), 2.34 (m, 2H), 2.00 (m, 2H)

Step 3:

A stirred solution of compound E9 (0.200 g, 0.68 mmol) in dimethylformamide (2 mL) was treated at room temperature with 5-amino-1-methyltetrazole (0.088 g, 0.89 mmol) followed by 4-(dimethylamino)pyridine (DMAP: 0.166 g, 136 mmol) and 1-propanephosphonic acid cyclic anhydride (PPAA: [50% in ethyl acetate] 2.4 mL, 4.08 mmol). The reaction mixture was heated to 100° C. for 30 mins in a microwave oven, then cooled and concentrated to dryness under reduced pressure. The residue was purified by preparative HPLC to obtain compound 1.011 (0.016 g).

1Hnmr (d6-DMSO): 12.35 (broad s, 1H), 9.38 (s, 1H), 4.20 (t, 2H), 3.92 (s, 3H), 2.38 (m, 2H), 2.02 (m, 2H)

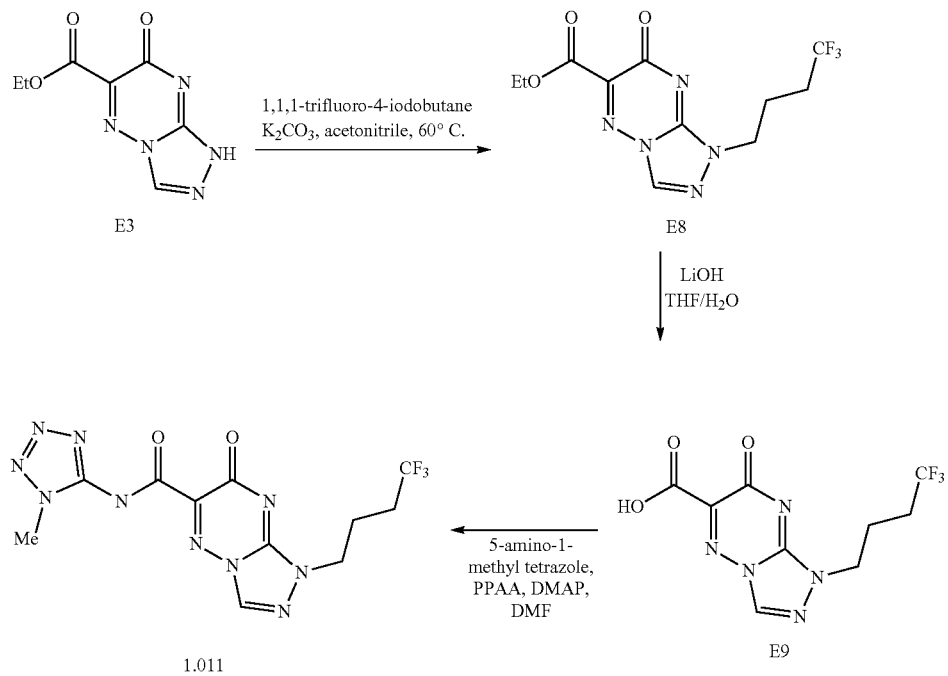 [SMILES: CCOC(=O)c1nn2cn[nH]c2nc1=O ; CCOC(=O)c1nn2cnn(CCCC(F)(F)F)c2nc1=O ; Cn1nnnc1NC(=O)c1nn2cnn(CCCC(F)(F)F)c2nc1=O ; O=C(O)c1nn2cnn(CCCC(F)(F)F)c2nc1=O]

PREPARATIVE EXAMPLE 5: PREPARATION OF COMPOUND 2.001

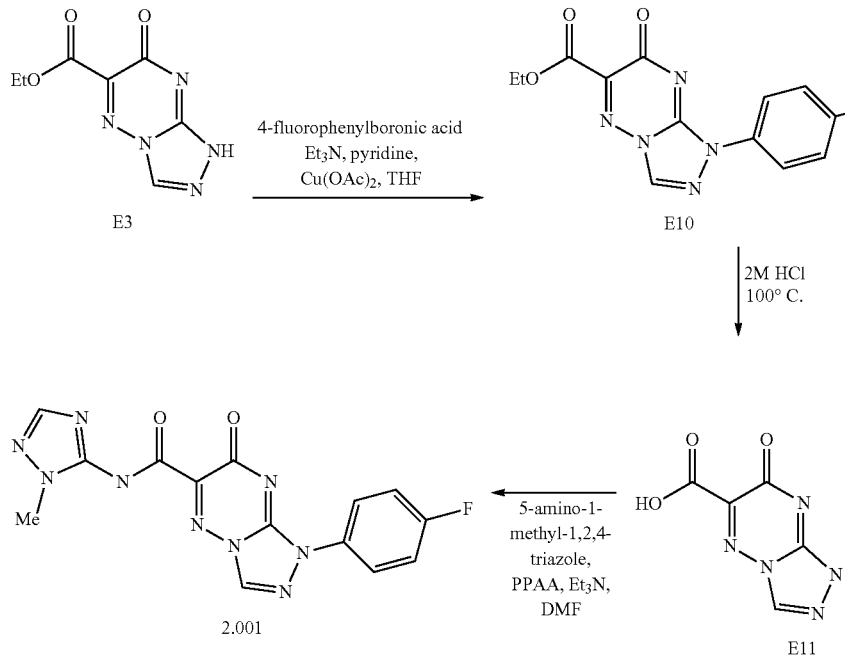

Step 1:

By a method analogous to that described in Preparative Example 1, Step 3, but using compound E3 (5.0 g, 23.9 mmol), 4-fluorophenylboronic acid (7.2 g, 35.83 mmol) triethylamine (10 mL, 71.76 mol), pyridine (5.7 mL, 71.76 mol), copper (II) acetate (8.6 g, 47.84 mmol) in THF (250 mL), compound E10 (1.40 g) was obtained.

1Hnmr (d6-DMSO): 9.49 (s, 1H), 8.00 (m, 2H), 7.47 (m, 2H), 4.39 (q, 2H), 1.32 (t, 3H)

Step 2:

By a method analogous to that described in Preparative Example 1, Step 4, compound E10 (1.40 g) was converted to compound E11 (0.77 g).

1Hnmr (d6-DMSO): 14.60 (broad s, 1H), 9.50 (s, 1H), 8.00 (m, 2H), 7.47 (t, 2H)

Step 3:

By a method analogous to that described in Preparative Example 1, Step 5, but using compound E11 (0.180 g, 0.654 mmol), 5-amino-1-methyl-1,2,4-triazole (0.77 g, 0.784 mmol), triethylamine (0.330 g, 0.5 ml, 3.27 mmol) and 1-propanephosphonic acid cyclic anhydride (PPAA: [50% in ethyl acetate] 1.9 mL, 3.27 mmol), and using dimethylformamide (DMF; 2 mL) as solvent, compound 2.001 (0.11 g) was obtained.

1Hnmr (d6-DMSO): 11.75 (broad s, 1H), 9.62 (broad s, 1H), 8.10-7.90 (m, 3H), 7.58-7.38 (m, 2H), 3.75 (s, 3H)

PREPARATIVE EXAMPLE 6: PREPARATION OF COMPOUND 3.001

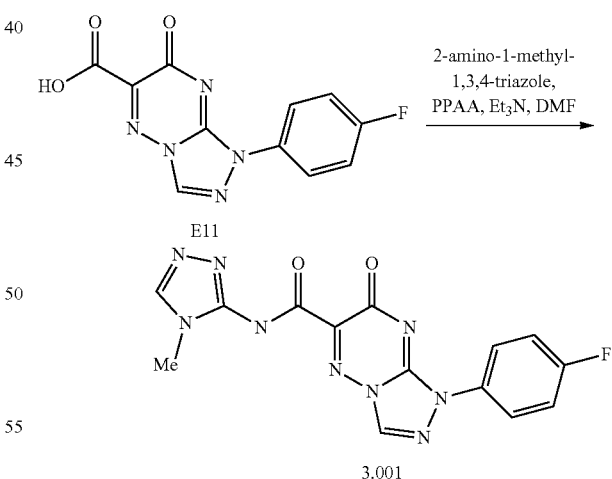

Step 1:

By a method analogous to that described in Preparative Example 1, Step 5, but using compound E11 (0.200 g, 0.726 mmol), 2-amino-1-methyl-1,3,4-triazole (0.100 g, 0.872 mmol), triethylamine (0.367 g, 0.5 ml, 3.633 mmol) and 1-propanephosphonic acid cyclic anhydride (PPAA: [50% in ethyl acetate] 2.0 mL, 3.633 mmol), and using dimethylformamide (DMF; 2 mL) as solvent, compound 3.001 (0.085 g) was obtained.

1Hnmr (d6-DMSO): 13.87 (broad s, 1H), 9.36 (broad s, 1H), 8.44 (broad s, 1H), 8.02 (m, 2H), 7.46 (m, 2H), 3.50 (s, 3H)

PREPARATIVE EXAMPLE 7: PREPARATION OF COMPOUND 1.037

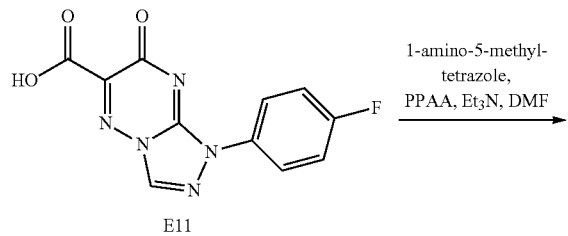

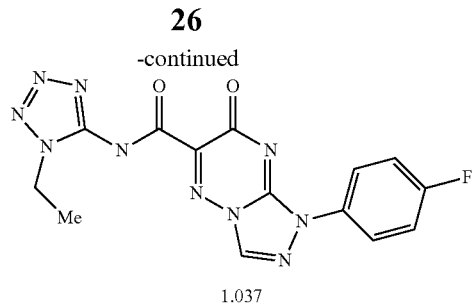

Step 1:
By a method analogous to that described in Preparative Example 1, Step 5, but using compound E11 (0.200 g, 0.726 mmol), 1-amino-5-ethyltetrazole (0.098 g, 0.872 mmol), triethylamine (0.367 g, 0.5 mL, 3.633 mmol) and 1-propanephosphonic acid cyclic anhydride (PPAA: [50% in ethyl acetate] 2.0 mL, 3.633 mmol), and using dimethylformamide (DMF; 2 mL) as solvent, compound 1.037 (0.15 g) was obtained.

1Hnmr (d6-DMSO): 12.25 (s, 1H), 9.65 (broad s, 1H), 8.02 (m, 2H), 7.52-7.48 (m, 2H), 4.34 (q, 2H), 1.46 (t, 3H)

TABLE 1

Examples of herbicidal compounds of the present invention.

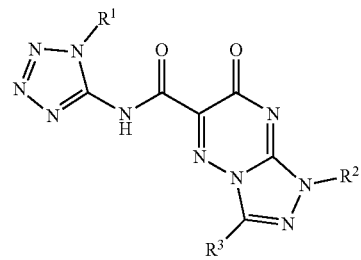

| Compound Number | $R^1$ | $R^2$ | $R^3$ | 1H-NMR |
|---|---|---|---|---|
| 1.001 | Methyl | Phenyl | H | (d6-DMSO): 3.98 (3H, s); 7.48 (1H, t); 7.64 (2H, t); 8.01 (2H, d); 9.67 (1H, s); 12.34 (1H, br s) |
| 1.002 | Methyl | 4-fluorophenyl- | H | (d6-DMSO): 12.33 (s, 1H), 9.67 (s, 1H), 8.02 (m, 2H), 7.50 (m, 2H), 3.98 (s, 3H) |
| 1.003 | Methyl | 4-methoxyphenyl- | H | (d6-DMSO): 12.38 (broad s, 1H), 9.63 (s, 1H), 7.86 (d, 2H), 7.18 (d, 2H), 3.98 (s, 3H), 3.84 (s, 3H) |
| 1.004 | Methyl | 4-SO$_2$Me-phenyl- | H | |
| 1.005 | Methyl | Methyl | H | |
| 1.006 | Methyl | Ethyl | H | |
| 1.007 | Methyl | n-Propyl | H | (d6-DMSO): 12.43 (s, 1H), 9.43 (broad s, 1H), 4.07 (t, 2H), 3.96 (s, 3H), 1.82 (m, 2H), 0.91 (t, 3H) |
| 1.008 | Methyl | n-Butyl | H | |
| 1.009 | Methyl | (CH$_3$)$_2$CHC$_2$H$_4$— | H | |
| 1.010 | Methyl | CH$_3$OC$_2$H$_4$— | H | (d6-DMSO): 12.35 (broad s, 1H), 9.43 (s, 1H), 4.27 (m, 2H), 3.96 (s, 3H), 3.75 (m, 2H), 3.25 (s, 3H) |
| 1.011 | Methyl | CF$_3$CH$_2$CH$_2$CH$_2$— | H | (d6-DMSO): 12.35 (broad s, 1H), 9.38 (s, 1H), 4.20 (t, 2H), 3.92 (s, 3H), 2.38 (m, 2H), 2.02 (m, 2H) |
| 1.012 | Methyl | Phenyl | Methyl | |
| 1.013 | Ethyl | Phenyl | H | (d6-DMSO): 12.27 (broad s, 1H), 9.67 (broad s, 1H), 8.01 (d, 2H), 7.64 (t, 2H), 7.48 (t, 1H), 4.35 (q, 2H), 1.47 (t, 3H) |
| 1.014 | n-Propyl | Phenyl | H | (d6-DMSO): 12.28 (s, 1H), 9.67 (s, 1H), 8.01 (d, 2H), 7.64 (t, 2H), 7.48 (t, 1H), 4.30 (t, 2H), 1.88 (q, 2H), 0.89 (t, 3H) |
| 1.015 | n-Butyl | Phenyl | H | |
| 1.016 | CH$_3$OC$_2$H$_4$— | Phenyl | H | |

TABLE 1-continued

Examples of herbicidal compounds of the present invention.

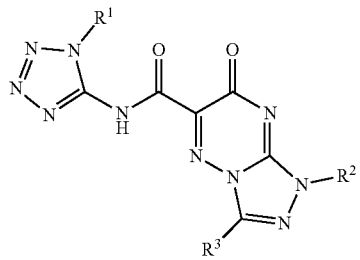

| Compound Number | R¹ | R² | R³ | 1H-NMR |
|---|---|---|---|---|
| 1.017 | —C₂H₄CF₃ | Phenyl | H | |
| 1.018 | Methyl | 3-chlorophenyl— | H | (d6-DMSO): 12.31 (s, 1H), 9.71 (s, 1H), 8.12 (broad s, 1H), 8.02 (broad d, 1H), 7.68 (broad t, 1H), 7.56 (broad d, 1H), 4.00 (s, 3H) |
| 1.019 | Methyl | 3-bromophenyl- | H | |
| 1.020 | Methyl | 3-CN-phenyl- | H | |
| 1.021 | Methyl | 3,4-dichlorophenyl- | H | |
| 1.022 | Methyl | 4-trifluoromethylphenyl- | H | (d6-DMSO): 12.29 (s, 1H), 9.73 (s, 1H), 8.31 (m, 2H), 8.04 (m, 2H), 3.99 (s, 3H) |
| 1.023 | Methyl | 4-CF₃O-phenyl- | H | |
| 1.024 | Methyl | 2-trifluoromethylphenyl- | H | |
| 1.025 | Methyl | 2-chlorophenyl- | H | |
| 1.026 | Methyl | 3-methylphenyl- | H | (d6-DMSO): 12.33 (broad s, 1H), 9.64 (s, 1H), 7.84-7.77 (m, 2H), 7.51 (t, 1H), 7.29 (d, 1H), 3.97 (s, 3H), 2.43 (s, 3H) |
| 1.027 | Phenyl | Phenyl | H | (d6-DMSO): 12.64 (s, 1H), 9.67 (s, 1H), 7.99 (d, 2H), 7.78-7.71 (m, 2H), 7.68-7.60 (m, 5H), 7.47 (t, 1H) |
| 1.028 | n-Propyl | 2-methylphenyl- | H | (d6-DMSO): 12.27 (broad s, 1H), 9.65 (s, 1H), 7.55-7.40 (m, 4H), 4.29 (t, 2H), 2.24 (s, 3H), 1.92-1.80 (m, 2H), 0.87 (t, 3H) |
| 1.029 | Methyl | 2,4-dimethylphenyl- | H | (d6-DMSO): 12.34 (broad s, 1H), 9.60 (s, 1H), 7.35 (d, 1H), 7.30 (s, 1H), 7.23 (d, 1H), 3.95 (s, 3H), 2.38 (s, 3H), 2.19 (s, 3H) |
| 1.030 | Methyl | 2-methylphenyl- | H | (d6-DMSO): 12.34 (broad s, 1H), 9.66 (s, 1H), 7.56-7.41 (m, 4H), 3.97 (s, 3H), 2.24 (s, 3H) |
| 1.031 | n-Propyl | n-Propyl | H | (d6-DMSO): 12.36 (broad s), 9.41 (s, 1H), 4.28 (t, 2H), 4.07 (t, 2H), 1.89-1.79 (m, 4), 0.94-0.85 (m, 6H) |
| 1.032 | Methyl | 2-methyl-4-methoxy-phenyl- | H | (d6-DMSO): 12.35 (broad s, 1H), 9.62 (broad s, 1H), 7.38 (broad d), 1H), 7.04 (broad s, 1H), 6.98 (broad d, 1H), 3.97 (s, 3H), 3.84 (s, 3H), 2.18 (s, 3H) |
| 1.033 | Ethyl | 3-chlorophenyl- | H | (d6-DMSO): 12.23 (broad s, 1H), 9.70 (s, 1H), 8.12 (broad s, 1H), 8.02 (broad d, 1H), 7.68 (broad t, 1H), 7.56 (broad d, 1H), 4.35 (m, 2H), 1.46 (m, 3H) |
| 1.034 | Ethyl | 4-methoxyphenyl- | H | (d6-DMSO): 12.81 (broad s, 1H), 9.61 (broad s, 1H), 7.85 (d, 2H), 7.18 (d, 2H), 4.33 (q, 2H), 3.84 (s, 3H), 1.46 (t, 3H) |
| 1.035 | n-Propyl | 4-methoxyphenyl- | H | (d6-DMSO): 12.30 (s, 1H), 9.62 (s, 1H), 7.85 (d, 2H), 7.18 (d, 2H), 4.30 (t, 2H), 3.83 (s, 3H), 1.87 (m, 2H), 0.88 (t, 3H) |
| 1.036 | n-Propyl | 3-methoxyphenyl- | H | (d6-DMSO): 12.25 (s, 1H), 9.66 (s, 1H), 7.64-7.52 (m, 3H), 7.06 (d, 1H), 4.30 (t, 2H), 3.85 (s, 3H), 1.91-1.85 (m, 2H), 0.89 (t, 3H) |
| 1.037 | Ethyl | 4-fluorophenyl- | H | (d6-DMSO): 12.25 (s, 1H), 9.65 (broad s, 1H), 8.02 (m, 2H), 7.52-7.48 (m, 2H), 4.34 (q, 2H), 1.46 (t, 3H) |
| 1.038 | n-Propyl | 4-fluorophenyl- | H | (d6-DMSO): 12.26 (broad s, 1H), 9.66 (s, 1H), 8.10-7.95 (m, 2H), 7.52-7.47 (m, 2H), 4.30 (t, 2H), 1.88 (m, 2H). 0.89 (t, 3H) |

TABLE 1-continued

Examples of herbicidal compounds of the present invention.

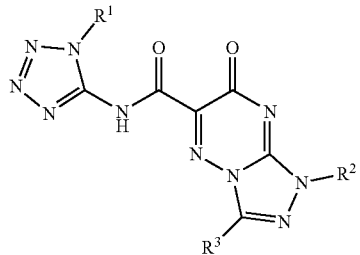

| Compound Number | R¹ | R² | R³ | 1H-NMR |
|---|---|---|---|---|
| 1.039 | n-Butyl | 4-fluorophenyl- | H | (d6-DMSO): 12.19 (s, 1H), 9.68 (s, 1H), 8.08-7.93 (m, 2H), 7.52-7.48 (m, 2H), 4.33 (t, 2H), 1.84 (m, 2H), 1.29 (m, 2H), 0.90 (t, 3H) |
| 1.040 | n-Butyl | 4-methoxyphenyl- | H | (d6-DMSO): 12.31 (s, 1H), 9.62 (s, 1H), 7.86 (d, 2H), 7.18 (d, 2H), 4.33 (t, 2H), 1.84 (m, 2H), 1.28 (m, 2H), 0.90 (t, 3H) |
| 1.041 | n-Butyl | 2,4dimethylphenyl- | H | |
| 1.042 | Ethyl | 4-trifluoromethylphenyl- | H | (d6-DMSO): 12.22 (s, 1H), 9.72 (s, 1H), 8.31 (d, 2H), 8.04 (d, 2H), 4.35 (q, 2H), 1.47 (t, 3H) |
| 1.043 | n-Propyl | 4-trifluoromethylphenyl- | H | (d6-DMSO): 12.23 (s, 1H), 9.71 (s, 1H), 8.31 (d, 2H), 8.04 (d, 2H), 4.31 (t, 2H), 1.88 (m, 2H), 0.89 (t, 3H) |
| 1.044 | n-Butyl | 4-trifluoromethylphenyl- | H | (d6-DMSO): 12.24 (s, 1H), 9.73 (s, 1H), 8.31 (d, 2H), 8.04 (d, 2H), 4.34 (t, 2H), 1.83 (m, 2H), 1.30 (m, 2H), 0.90 (t, 3H) |
| 1.045 | Ethyl | 2,4dimethylphenyl- | H | (d6-DMSO): 12.28 (broad s, 1H), 9.57 (broad s, 1H), 7.34-7.23 (m, 3H), 4.31 (m, 2H), 2.38 (s, 3H), 2.18 (s, 3H), 1.43 (m, 3H) |
| 1.046 | Ethyl | 3-methylphenyl- | H | (d6-DMSO): 12.27 (s, 1H), 9.66 (s, 1H), 7.85-7.75 (m, 2H), 7.52 (t, 1H), 7.29 (d, 1H), 4.35 (q, 2H), 2.44 (s, 3H), 1.47 (t, 3H) |
| 1.047 | i-Butyl | Phenyl | H | |
| 1.048 | n-Propyl | 3-chlorophenyl- | H | |
| 1.049 | n-Butyl | 3-chlorophenyl- | H | |
| 1.050 | n-Propyl | 4-methoxyphenyl- | H | |
| 1.051 | n-Butyl | 4-methoxyphenyl- | H | |
| 1.052 | n-Butyl | 3-methylphenyl- | H | |
| 1.053 | n-Propyl | 3-methylphenyl- | H | |
| 1.054 | Ethyl | 2-methylphenyl | H | |
| 1.055 | n-Butyl | 2-methylphenyl | H | |
| 1.056 | n-Propyl | 2,4dimethylphenyl- | H | |
| 1.057 | n-Propyl | 2-methyl-4-methoxyphenyl- | H | |
| 1.058 | Ethyl | 2-methyl-4-methoxyphenyl- | H | |
| 1.059 | n-Butyl | 2-methyl-4-methoxyphenyl- | H | |
| 1.060 | n-Butyl | 3-methoxyphenyl- | H | |
| 1.061 | Ethyl | 3-methoxyphenyl- | H | |
| 1.062 | Methyl | 3-methoxyphenyl- | H | |
| 1.063 | n-Butyl | $CH_3OCH_2CH_2$— | H | |
| 1.064 | Ethyl | n-propyl | H | |
| 1.065 | n-butyl | n-propyl | H | |
| 1.066 | n-Propyl | $CH_3OCH_2CH_2$— | H | |
| 1.067 | Ethyl | $CH_3OCH_2CH_2$— | H | |
| 1.068 | Ethyl | $CF_3CH_2CH_2CH_2$— | H | |
| 1.069 | n-Propyl | $CF_3CH_2CH_2CH_2$— | H | |
| 1.070 | n-Butyl | $CF_3CH_2CH_2CH_2$— | H | |

TABLE 2

Examples of herbicidal compounds of the present invention.

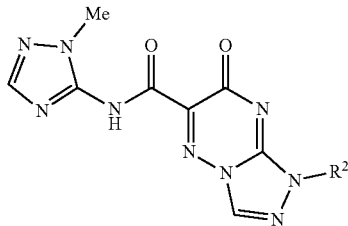

| Compound Number | R² | 1H-NMR |
|---|---|---|
| 2.001 | 4-fluorophenyl- | (d6-DMSO): 11.75 (broad s, 1H), 9.62 (broad s, 1H), 8.10-7.90 (m, 3H), 7.58-7.38 (m, 2H), 3.75 (s, 3H) |
| 2.002 | 2-methylphenyl- | |
| 2.003 | 2,4-dimethylphenyl- | |
| 2.004 | CF₃CH₂CH₂CH₂— | |

TABLE 3

Examples of herbicidal compounds of the present invention.

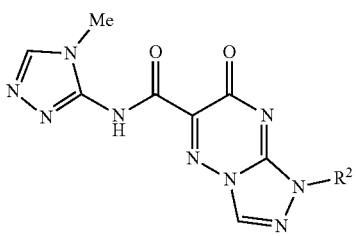

| Compound Number | R² | 1H-NMR |
|---|---|---|
| 3.001 | 4-fluorophenyl- | (d6-DMSO): 13.87 (broad s, 1H), 9.36 (broad s, 1H), 8.44 (broad s, 1H), 8.02 (m, 2H), 7.46 (m, 2H), 3.50 (s, 3H) |
| 3.002 | 2-methylphenyl- | |
| 3.003 | 2,4-dimethylphenyl- | |
| 3.004 | CF₃CH₂CH₂CH₂— | |

TABLE 4

Examples of herbicidal compounds of the present invention.

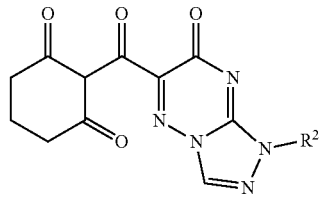

| Compound Number | R² | 1H-NMR |
|---|---|---|
| 4.001 | Phenyl | (d6-DMSO): 1.93-1.96 (2H, m); 2.33-2.60 (4H, m); 7.45 (1H, t); 7.61 (2H, t), 7.80 (2H, d); 9.42 (1H, s) |
| 4.002 | 4-fluorophenyl- | (d6-DMSO): 9.41 (1H, s), 8.02 (m, 2H), 7.47 (m, 2H), 2.57-2.50 (m, 4H), 1.95-1.91 (m, 2H) |
| 4.003 | 4-methoxyphenyl- | |
| 4.004 | 4-SO₂Me-phenyl- | |
| 4.005 | n-Propyl | |
| 4.006 | CH₃OC₂H₄— | |
| 4.007 | CF₃CH₂CH₂CH₂— | |
| 4.008 | 4-trifluoromethylphenyl- | (d6-DMSO): 9.47 (s, 1H), 8.31 (m, 2H), 8.01 (m, 2H), 2.62-2.42 (m, 4H), 1.98-1.89 (m, 2H) |
| 4.009 | 3-chlorophenyl- | (d6-DMSO): 9.45 (s, 1H), 8.13 (m, 1H), 8.01 (broad d, 1H), 7.65 (t, 1H), 7.52 (broad d, 1H), 2.65-2.47 (m, 4H), 1.98-1.87 (m, 2H) |
| 4.010 | 3-methoxyphenyl- | (d6-DMSO): 9.41 (s, 1H), 7.66-7.57 (m, 2H), 7.52 (t, 1H), 7.03 (dd, 1H), 3.84 (s, 3H), 2.66-2.52 (m, 4H), 1.98-1.92 (m, 2H) |
| 4.011 | 3-methylphenyl- | |
| 4.012 | 2-methyl-4-methoxyphenyl- | |
| 4.013 | 2-methylphenyl- | |
| 4.014 | 2,4dimethylphenyl- | |

TABLE 5

Examples of herbicidal compounds of the present invention.

| Compound Number | R² | 1H-NMR |
|---|---|---|
| 5.001 | Phenyl | |
| 5.002 | 4-fluorophenyl- | |
| 5.003 | 4-methoxyphenyl- | |
| 5.004 | 4-SO₂Me-phenyl- | |
| 5.005 | n-Propyl | |
| 5.006 | CH₃OC₂H₄— | |
| 5.007 | CF₃CH₂CH₂CH₂— | |
| 5.008 | 4-trifluoromethylphenyl- | (CDCl3): 8.40-8.34 (m, 3H), 7.76 (d, 2H), 3.15 (m, 1H), 2.94 (m, 1H), 2.35-1.50 (complex, 6H) |
| 5.009 | 3-chlorophenyl- | |
| 5.010 | 3-methylphenyl- | |
| 5.011 | 3-methoxyphenyl- | |
| 5.012 | 2-methylphenyl- | |
| 5.013 | 2,4dimethylphenyl- | |
| 5.014 | 2-methyl-4-methoxyphenyl- | |

TABLE 6

Examples of herbicidal compounds of the present invention.

| Compound Number | R² | 1H-NMR |
|---|---|---|
| 6.001 | 3-methylphenyl- | (CDCl3): 15.56 (s, 1H), 8.30 (s, 1H), 7.91-7.78 (m, 2H), 7.38 (broad t, 1H), 7.18 (broad d, 1H), 2.83-2.76 (m, 1H), 2.61-2.38 (m, 2H), 2.43 (s, 3H), 2.35-2.10 (m, 2H) |
| 6.002 | 4-fluorophenyl- | |
| 6.003 | 4-methoxyphenyl- | |
| 6.004 | 4-trifluoromethylphenyl- | |
| 6.005 | 3-chlorophenyl- | |
| 6.006 | 3-methoxyphenyl- | |
| 6.007 | 2-methylphenyl- | |
| 6.008 | 2,4-dimethylphenyl- | |
| 6.009 | 2-methyl-4-methoxyphenyl- | |
| 6.010 | Phenyl | |
| 6.011 | n-Propyl | |
| 6.012 | CH₃OCH₂CH₂— | |
| 6.013 | CF₃CH₂CH₂CH₂— | |

TABLE 7

Examples of herbicidal compounds of the present invention.

| Compound Number | Structure |
|---|---|
| 7.001 | *(structure image)* |
| 7.002 | *(structure image)* |
| 7.003 | *(structure image)* |
| 7.004 | *(structure image)* |
| 7.005 | *(structure image)* |

TABLE 7-continued

Examples of herbicidal compounds of the present invention.

| Compound Number | Structure |
|---|---|
| 7.006 | *(structure image)* |
| 7.007 | *(structure image)* |

BIOLOGICAL EXAMPLES

Seeds of a variety of test species are sown in standard soil in pots (*Lolium perenne* (LOLPE), *Solanum nigrum* (SOLNI), *Amaranthus retoflexus* (AMARE), *Setaria faberi* (SETFA), *Echinochloa crus-galli* (ECHCG), *Ipomoea hederacea* (IPOHE)). After cultivation for one day (pre-emergence) or after 8 days cultivation (post-emergence) under controlled conditions in a glasshouse (at 24/16° C., day/night; 14 hours light; 65% humidity), the plants are sprayed with an aqueous spray solution derived from the formulation of the technical active ingredient in acetone/water (50:50) solution containing 0.5% Tween 20 (polyoxyethelyene sorbitan monolaurate, CAS RN 9005-64-5). Compounds are applied at 1000 g/h. The test plants are then grown in a glasshouse under controlled conditions in a glasshouse (at 24/16° C., day/night; 14 hours light; 65% humidity) and watered twice daily. After 13 days for pre and post-emergence, the test is evaluated for the percentage damage caused to the plant. The biological activities are shown in the following table on a five point scale (5=80-100%; 4=60-79%; 3=40-59%; 2=20-39%; 1=0-19%).

TABLE B1

| Compound | POST Application | | | | | | PRE Application | | | | | |
|---|---|---|---|---|---|---|---|---|---|---|---|---|
| | LOLPE | SOLNI | AMARE | SETFA | ECHCG | IPOHE | LOLPE | SOLNI | AMARE | SETFA | ECHCG | IPOHE |
| 1.001 | 3 | 5 | 5 | 5 | 5 | 5 | 3 | 5 | 5 | 5 | 5 | 4 |
| 1.002 | 5 | 5 | 5 | 5 | 5 | 5 | 4 | 5 | 5 | 5 | 5 | 5 |
| 1.003 | 4 | 5 | 5 | 5 | 5 | 5 | 4 | 5 | 5 | 5 | 5 | 5 |
| 1.007 | 3 | 5 | 5 | 5 | 5 | 5 | 4 | 5 | 5 | 5 | 5 | 4 |
| 1.010 | 3 | 4 | 4 | 4 | 5 | 4 | 1 | 3 | 4 | 3 | 3 | 4 |
| 1.011 | 3 | 4 | 5 | 5 | 5 | 5 | 2 | 4 | 5 | 5 | 4 | 4 |
| 1.013 | 5 | 5 | 5 | 5 | 5 | 5 | 5 | 5 | 5 | 5 | 5 | 5 |
| 1.014 | 5 | 5 | 5 | 5 | 5 | 5 | 5 | 5 | 5 | 5 | 5 | 5 |
| 1.018 | 4 | 5 | 5 | 5 | 5 | 5 | 3 | 5 | 4 | 5 | 5 | 5 |

TABLE B1-continued

| Compound | POST Application | | | | | | PRE Application | | | | | |
|---|---|---|---|---|---|---|---|---|---|---|---|---|
| | LOLPE | SOLNI | AMARE | SETFA | ECHCG | IPOHE | LOLPE | SOLNI | AMARE | SETFA | ECHCG | IPOHE |
| 1.022 | 3 | 5 | 5 | 5 | 5 | 4 | 4 | 5 | 5 | 5 | 5 | 4 |
| 1.026 | 4 | 5 | 5 | 5 | 5 | 5 | 5 | 5 | 5 | 5 | 5 | 4 |
| 1.027 | 2 | 5 | 4 | 2 | 1 | 3 | 1 | 5 | 5 | 2 | 1 | 4 |
| 1.028 | 5 | 5 | 5 | 5 | 5 | 5 | 5 | 5 | 5 | 5 | 5 | 5 |
| 1.030 | 4 | 5 | 5 | 5 | 5 | 5 | 4 | 5 | 5 | 5 | 5 | 5 |
| 1.031 | 5 | 5 | 5 | 5 | 5 | 5 | 5 | 5 | 5 | 4 | 5 | 5 |
| 1.032 | 4 | 5 | 5 | 4 | 5 | 5 | 5 | 5 | 5 | 5 | 5 | 5 |
| 1.033 | 4 | 5 | 5 | 5 | 5 | 5 | 5 | 5 | 5 | 4 | 5 | 2 |
| 1.034 | 4 | 5 | 5 | 5 | 5 | 5 | 4 | 5 | 5 | 5 | 5 | 3 |
| 1.035 | 5 | 5 | 4 | 4 | 5 | 5 | 5 | 5 | 5 | 5 | 5 | 5 |
| 1.036 | 5 | 5 | 5 | 5 | 4 | 5 | 5 | 5 | 5 | 5 | 5 | 4 |
| 1.037 | 4 | 5 | 5 | 5 | 5 | 4 | 4 | 5 | 5 | 5 | 5 | 5 |
| 1.038 | 5 | 5 | 5 | 5 | 5 | 5 | 4 | 5 | 5 | 5 | 5 | 5 |
| 1.039 | 5 | 5 | 5 | 5 | 5 | 5 | 5 | 5 | 5 | 5 | 5 | 4 |
| 1.040 | 5 | 5 | 4 | 4 | 3 | 5 | 5 | 5 | 3 | 5 | 5 | 5 |
| 1.042 | 3 | 5 | 4 | 4 | 3 | 4 | 4 | 5 | 5 | 5 | 5 | 4 |
| 1.043 | 3 | 5 | 5 | 4 | 1 | 4 | 3 | 5 | 4 | 5 | 2 | 3 |
| 1.044 | 3 | 5 | 4 | 3 | 1 | 5 | 3 | 5 | 3 | 3 | 2 | 3 |
| 1.045 | 5 | 5 | 5 | 5 | 5 | 5 | 5 | 5 | 5 | 4 | 5 | 5 |
| 1.046 | NT | NT | 5 | 5 | 5 | 5 | NT | NT | 5 | 5 | 5 | 5 |
| 2.001 | 4 | 5 | 5 | 5 | 4 | 5 | 3 | 5 | 5 | 5 | 5 | 4 |
| 3.001 | 1 | 5 | 3 | 1 | 1 | 1 | 1 | 1 | 3 | 1 | 1 | 1 |
| 4.001* | 1 | NT | 5 | 5 | 5 | 5 | 2 | NT | 5 | 1 | 5 | 1 |
| 4.002 | 5 | 5 | 5 | 5 | 5 | 5 | 4 | 5 | 5 | 5 | 5 | 5 |
| 4.008 | NT | NT | 4 | 5 | 5 | 5 | NT | NT | 5 | 5 | 5 | 5 |
| 4.009 | NT | NT | 5 | 5 | 5 | 5 | NT | NT | 5 | 5 | 5 | 5 |
| 4.010 | 4 | 5 | 5 | 5 | 5 | 5 | 5 | 5 | 5 | 5 | 5 | 5 |
| 5.008 | NT | NT | 5 | 5 | 5 | 5 | NT | NT | 5 | 5 | 5 | 5 |
| 6.001 | NT | NT | 5 | 5 | 5 | 5 | NT | NT | 5 | 4 | 5 | 5 |

*Applied at 250 g/ha.
NT = Not tested.

The invention claimed is:
1. A compound of Formula (I):

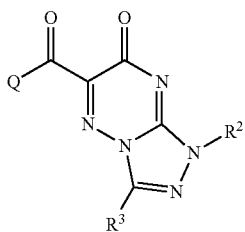

or an agronomically acceptable salt thereof, wherein:

Q is Q1 or Q2

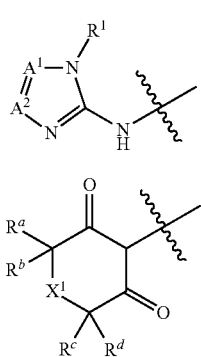

$A^1$ and $A^2$ are independently selected from CH and N, wherein $A^1$ and $A^2$ are not both CH;

$X^1$ is selected from the group consisting of O, C(O) and $(CR^eR^f)$;

$R^a$, $R^b$, $R^c$, $R^d$, $R^e$ and $R^f$ are each independently selected from the group consisting of hydrogen and $C_1$-$C_4$alkyl wherein $R^a$ and $R^c$ may together form a $C_1$-$C_3$alkylene chain;

$R^1$ is selected from the group consisting of $C_1$-$C_6$alkyl-, $C_1$-$C_6$haloalkyl-, $C_1$-$C_6$alkoxy-$C_1$-$C_3$alkyl-, $C_1$-$C_6$haloalkoxy-$C_1$-$C_3$alkyl- and phenyl wherein the phenyl is optionally substituted by one or more substituents selected from the group consisting of halogen, $C_1$-$C_6$alkyl-, $C_1$-$C_6$alkoxy-, nitro and cyano;

$R^2$ is selected from the group consisting of $C_1$-$C_6$alkyl-, $C_1$-$C_6$ haloalkyl, $C_2$-$C_6$alkenyl-, $C_2$-$C_6$haloalkenyl-, $C_2$-$C_6$alkynyl-, $C_2$-$C_6$haloalkynyl-, $C_1$-$C_6$ alkoxyC$_1$-$C_3$alkyl-, $C_1$-$C_6$haloalkoxyC$_1$-$C_3$alkyl-, $C_1$-$C_6$alkoxyC$_2$-$C_3$alkoxyC$_1$-$C_3$alkyl-, —(CH$_2$)$_n$—C$_3$-$C_6$cycloalkyl, benzyl, phenyl and a five or six-membered heteroaryl, the heteroaryl containing from one to three heteroatoms each independently selected from the group consisting of oxygen, nitrogen and sulphur, and wherein the benzyl, phenyl or heteroaryl may be optionally substituted by one or more substituents selected from the group consisting of halogen, $C_1$-$C_6$alkyl-, $C_2$-$C_6$alkenyl-, $C_2$-$C_6$alkynyl-, $C_1$-$C_6$haloalkyl-, $C_1$-$C_6$alkoxy-, $C_1$-$C_6$alkoxyC$_1$-$C_3$alkyl-, $C_1$-$C_6$alkoxyC$_1$-$C_3$alkoxy-, $C_1$-$C_6$haloalkoxy-, $C_1$-$C_6$alkyl-S(O)p-, cyano and nitro;

$R^3$ is selected from the group consisting of hydrogen, $C_1$-$C_4$ alkyl and $C_1$-$C_4$ haloalkyl;

n=1, 2 or 3; and p=0, 1 or 2.

2. A compound according to claim 1, wherein Q is Q1 and $A^1$ and $A^2$ are both N.

3. A compound according to claim 1, wherein $R^1$ is selected from the group consisting of methyl, ethyl and n-propyl.

4. A compound according to claim 1, wherein Q is Q2, $X^1$ is $CR^eR^f$ and $R^a$, $R^b$, $R^c$, $R^d$, $R^e$ and $R^f$ are hydrogen.

5. A compound according to claim 1, wherein $R^2$ is selected from the group consisting of $C_1$-$C_6$alkyl- and $C_1$-$C_6$haloalkyl-.

6. A compound according to claim 1, wherein $R^2$ is phenyl which is optionally substituted by one or more substituents selected from the group consisting of halogen, $C_1$-$C_6$alkyl-, $C_1$-$C_6$alkoxy- and $C_1$-$C_6$alkyl-S(O)p-.

7. A compound according to claim 1, wherein $R^3$ is hydrogen.

8. A compound according to claim 2, wherein $R^1$ is selected from the group consisting of methyl, ethyl and n-propyl.

9. A compound according to claim 8, wherein $R^3$ is hydrogen.

10. A compound according to claim 9, wherein $R^2$ is phenyl which is optionally substituted by one or more substituents selected from the group consisting of halogen, $C_1$-$C_6$alkyl-, $C_1$-$C_6$haloalkyl-, $C_1$-$C_6$alkoxy- and $C_1$-$C_6$alkyl-S(O)p-.

11. A compound according to claim 9, wherein $R^2$ is selected from the group consisting of $C_1$-$C_6$alkyl- and $C_1$-$C_6$haloalkyl-.

12. A herbicidal composition comprising a compound according to claim 1 and an agriculturally acceptable formulation adjuvant.

13. A herbicidal composition according to claim 12, further comprising at least one additional pesticide.

14. A herbicidal composition according to claim 13, wherein the additional pesticide is a herbicide or herbicide safener.

15. A method of controlling weeds at a locus comprising application to the locus of a weed controlling amount of a composition according to claim 12.

* * * * *